(12) United States Patent
Kroth et al.

(10) Patent No.: US 10,865,207 B2
(45) Date of Patent: Dec. 15, 2020

(54) COMPOUNDS FOR IMAGING TAU PROTEIN AGGREGATES

(71) Applicants: AC IMMUNE S.A., Lausanne (CH);
LIFE MOLECULAR IMAGING SA, Matran (CH)

(72) Inventors: Heiko Kroth, Ecublens (CH); Jérôme Molette, Prevessin Moens (FR); Hanno Schieferstein, Berlin (DE); Andre Müller, Berlin (DE); Heribert Schmitt-Willich, Berlin (DE); Mathias Berndt, Berlin (DE); Felix Oden, Berlin (DE)

(73) Assignees: AC IMMUNE S.A., Lausanne (CH);
LIFE MOLECULAR IMAGING SA, Matran (CH)

( * ) Notice: Subject to any disclaimer, the term of this patent is extended or adjusted under 35 U.S.C. 154(b) by 0 days.

(21) Appl. No.: 16/319,808

(22) PCT Filed: Jul. 21, 2017

(86) PCT No.: PCT/EP2017/068500
§ 371 (c)(1),
(2) Date: Jan. 22, 2019

(87) PCT Pub. No.: WO2018/015546
PCT Pub. Date: Jan. 25, 2018

(65) Prior Publication Data
US 2019/0263817 A1 Aug. 29, 2019

(30) Foreign Application Priority Data
Jul. 22, 2016 (EP) ..................... 16180905

(51) Int. Cl.
| | | |
|---|---|---|
| *A61K 51/00* | (2006.01) | |
| *A61M 36/14* | (2006.01) | |
| *C07D 471/14* | (2006.01) | |
| *G01N 33/60* | (2006.01) | |
| *G01N 33/68* | (2006.01) | |
| *A61K 51/04* | (2006.01) | |
| *C07B 59/00* | (2006.01) | |

(52) U.S. Cl.
CPC ........ *C07D 471/14* (2013.01); *A61K 51/0455* (2013.01); *C07B 59/002* (2013.01); *G01N 33/60* (2013.01); *G01N 33/6896* (2013.01); *G01N 2800/2821* (2013.01); *G01N 2800/2835* (2013.01); *G01N 2800/7047* (2013.01)

(58) Field of Classification Search
CPC .............. C07D 471/14; A61K 51/0455; C07B 59/002; G01N 33/60; G01N 33/6896; G01N 2800/2821; G01N 2800/2835; G01N 2800/7047
USPC ....................................................... 424/1.89
See application file for complete search history.

(56) References Cited

U.S. PATENT DOCUMENTS 8,691,187 B2 4/2014 Szardenings
8,932,557 B2 1/2015 Chen

FOREIGN PATENT DOCUMENTS

| WO | 2009102498 A1 | 8/2009 | |
|---|---|---|---|
| WO | 2011119565 A1 | 9/2011 | |
| WO | 2012067863 A1 | 5/2012 | |
| WO | 2012068072 A1 | 5/2012 | |
| WO | 2013176698 A1 | 11/2013 | |
| WO | 2014026881 A1 | 2/2014 | |
| WO | 2014177458 A1 | 11/2014 | |
| WO | 2014187762 A1 | 11/2014 | |
| WO | 2015044095 A1 | 4/2015 | |
| WO | 2015052105 A1 | 4/2015 | |
| WO | 2015110263 A1 | 7/2015 | |
| WO | 2015173225 A1 | 11/2015 | |
| WO | 2015188368 A1 | 12/2015 | |
| WO | WO-2015191506 A2 * | 12/2015 | ........... C07D 471/04 |
| WO | 2016057812 A1 | 4/2016 | |
| WO | 2016124508 A1 | 8/2016 | |

OTHER PUBLICATIONS

International Search Report and Written Opinion issued by the European Patent Office (EPO) dated Nov. 7, 2017 for PCT/EP2017/068500.

A. Andreadis et al., "Structure and novel exons of the human tau gene.," Biochemistry, No. 31, pp. 10626-10633, 1992.

(Continued)

*Primary Examiner* — Michael G. Hartley
*Assistant Examiner* — Sean R Donohue
(74) *Attorney, Agent, or Firm* — F. Brent Nix, Esq.; Johnson, Marcou, Isaacs & Nix, LLC

(57) ABSTRACT

The present invention relates to novel compounds of the formula (I)

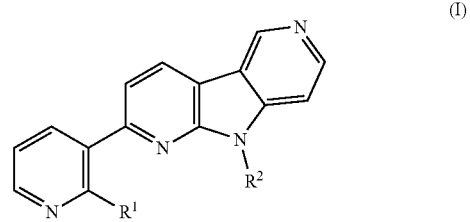

that can be employed in the selective Tau detection of disorders and abnormalities associated with Tau aggregates such as Alzheimer's disease and other tauopathies using Positron Emission Tomography (PET) Imaging.

26 Claims, 3 Drawing Sheets

(56) References Cited

OTHER PUBLICATIONS

M. Ariza et al., "Tau Positron Emission Tomography (PET) Imaging: Past, Present, and Future," J Med Chem, vol. 58, Issue 11, pp. 4365-4382, Publication Date (Web): Feb. 11, 2015.
DT. Chien DT et al., "Early Clinical PET Imaging Results with the Novel PHF-Tau Radioligand [F18]-T808," J Alzheimers Dis., vol. 38, pp. 171-184, 2014.
Felipe, Gomez et al., "Quantitative assessment of [18F]AV-1451 distribution in AD, PSP and PiD Post-Mortem Brain Tissue Sections relative to that of the anti-Tau antibody AT8," Journal of Nuclear Medicine, vol. 57, Supplement 2:348, May 1, 2016.
J.A., Hardy et al., "Alzheimer's disease: the amyloid cascade hypothesis," Science, vol. 256, pp. 184-185, Apr. 10, 1992.
A., Jovalekic et al., "New protein deposition tracers in the pipeline," EJNMMI Radiopharmacy and Chemistry, vol. 1, Issue 11, pp. 1-12, 2016.
L. Cai et al., "Chemistry with [18F]Fluoride Ion," Eur. J. Org. Chem, pp. 2853-2873, 2008.
VJ, Lowe et al., "An autoradiographic evaluation of AV-1451 Tau PET in dementia," Acta Neuropathologica Communications, vol. 4, Issue 58, 2016.
Timothy M. Shoup et al., "A Concise Radiosynthesis of the Tau Radiopharmaceutical, [18F]T807," J. Labelled Comp. Radiopharm., vol. 56, Issue 14, pp. 736-740, Dec. 2013.
M. Tolnay et al., "The Neuropathological Spectrum of Neurodegenerative Tauopathies," IUBMB Life, vol. 55, Issue 6, pp. 299-305, Jun. 2003.
Marta Marquie et al.,"Validating novel Tau Positron Emission Tomography Tracer [F-18]-AV-1451 (T807) on postmortem Brain Tissue," Annals of Neurology, vol. 78, Issue 5, pp. 787-800, Nov. 2015.
E.S. Musiek et al., "Three Dimensions of the Amyloid Hypothesis: Time, Space, and Wingmen," Nature Neurosciences, vol. 18, Issue 6, pp. 800-806, Jun. 2015.
K.P. Ng et al., "Monoamine oxidase B inhibitor, selegiline, reduces 18F-THK5351 uptake in the human brain," Alzheimer's Research and Therapy, vol. 9, Issue 25, pp. 1-9, 2017.
K. Sanders et al., "Characterization of tau positron emission tomography tracer AV1451 binding to postmortem tissue in Alzheimer's disease, primary tauopathies, and other dementias," Alzheimers Dementia vol. 12, Issue 11, pp. 116-1124, 2016.
Maliha Shah et al., "Molecular Imaging Insights into Neurodegeneration: Focus on Tau PET Radiotracers," J Nucl Med., vol. 55, Issue 6, pp. 871-874, Mar. 13, 2014.
Ruben Smith et al., "Tau neuropathology correlates with FDG-PET, but nor with AV-1451-PET, in progressive supranuclear palsy," Acta Neuropathologica, vol. 133, Issue 1, pp. 149-151, 2017.
Ruben Smith et al., "Increased basal ganglia binding of 18F-AV-1451 in patients with progressive supranuclear palsy," Movement disorders, vol. 32, Issue 1, pp. 108-114, Jan. 2017.
C. Vermeiren et al., "T807, a reported selective tau tracer, binds with nanomolar affinity to monoamine oxidase A," Alzheimers & Dementia, vol. 11, Issue 7, Supplement P1-2, Jul. 22, 2015.
Zrein, M. et al., "Assessment of a New Immunoassay for Serological Confirmation and Discrimination of Human T-Cell Lymphotropic Virus Infections", Clin. Diagn. Lab. Immunol., vol. 5, No. 1, pp. 45-49, Accepted: Oct. 22, 1997.
Stang, P. J., et al., "Perfluoroalkanesulfonic Esters: Methods of Preparation and Applications in Organic Chemistry," Synthesis, pp. 85-125, 1982.
Carey and Sundberg, Organische Synthese, (1995), p. 279-281.
Netscher, Thomas, "Sulfonate leaving groups for nucleophilic substitution reactions—Improved structures and procedures," Recent Res. Devel. Organic Chem., 2003, vol. 7, pp. 71-83, 2003.
Coenen, H.H., "Fluorine-18 Labeling Methods: Features and Possibilities of Basic Reactions", pp. 15-50, 2006.
Angelini, G. et al., "Nucleophilic Aromatic Substitution of Activated Cationic Groups by 18F-Labeled Fluoride. A Useful Route XI NO-Carrier-Added (NCA) 18F-Labeled Aryl Fluorides", J. Fluorine Chem., vol. 27, pp. 177-191, Accepted: Jun. 20, 1984.
"Human Amyloid Imaging Meeting," Alzforum, Networking for a Cure, pp. 1-23, 2015.
Kroth, et al., "Discovery and preclinical characterization of [18F]PI-2620, a next-generation tau PET tracer for the assessment of tau pathology in Alzheimer's disease and other tauopathies", European Journal of Nuclear Medicine and Molecular Imaging, vol. 46, pp. 2178-2189, Jul. 1, 2019.

* cited by examiner

<sup>18</sup>F-1

<sup>18</sup>F-2

<sup>18</sup>F-4

COMPOUNDS FOR IMAGING TAU PROTEIN AGGREGATES

CROSS REFERENCE TO RELATED APPLICATIONS

This application is a 35 U.S.C. § 371 national stage of International Application No. PCT/EP2017/068500 filed on Jul. 21, 2017, and published in English under PCT Article 21(2), which claims the benefit of European Patent Application No. 16180905.8 filed Jul. 22, 2016. The entire contents of the above-identified priority applications are hereby fully incorporated herein by reference.

FIELD OF INVENTION

The present invention relates to novel compounds of the formula (I) that can be employed in the selective detection of disorders and abnormalities associated with Tau aggregates such as Alzheimer's disease (AD) and other tauopathies, for example, using Positron Emission Tomography (PET) imaging. The present invention also refers to intermediates which can be used in the production of such imaging compounds. Diagnostic compositions as well as methods of imaging or diagnosing using the above compounds and kits which are useful for preparing a radiopharmaceutical preparation are also subject of the present invention.

BACKGROUND

Alzheimer's disease is a neurological disorder primarily thought to be caused by amyloid plaques, an extracellular accumulation of abnormal deposit of amyloid-beta (Aβ) aggregates in the brain or in the eyes. The other major neuropathological hallmarks in AD are the intracellular neurofibrillary tangles (NFT) that originate by the aggregation of the hyperphosphorylated Tau (Tubulin associated unit) protein, phosphorylated Tau or pathological Tau and its conformers. AD shares this pathology with many neurodegenerative tauopathies, in particularly with specified types of frontotemporal dementia (FTD). In AD brain, Tau pathology (tauopathy) develops later than amyloid pathology, but it is still discussed controversially if Aβ protein is the causative agent in AD which constitutes the essence of the so-called amyloid cascade hypothesis (Hardy et al., Science 1992, 256, 184-185, and most recently, Musiek et al., Nature Neurosciences 2015, 18(6), 800-806, "Three dimensions of the amyloid hypothesis: time, space and 'wingmen'").

Presently, the only definite way to diagnose AD is to identify plaques and tangles in brain tissue by histological analysis of biopsy or autopsy materials after the death of the individual. Beside AD, Tau plays an important role in other (non-AD) neurodegenerative diseases. Such non-AD tauopathies include, for example, supranuclear palsy (PSP), Pick's disease (PiD) and corticobasal degeneration (CBD).

Therefore, there is a great deal of interest in detection of Tau pathology in vivo. Tau PET imaging promises novel insights into deposition of Tau aggregates in the human brain and might allow to non-invasively examine the degree of Tau pathology, quantify changes in Tau deposition over time, assess its correlation with cognition and analyze the efficacy of an anti-Tau therapy. For recent reviews see Shah et al., J Nucl Med. 2014, 55(6), 871-874: "Molecular Imaging Insights into Neurodegeneration: Focus on Tau PET Radiotracers", Jovalekic et al., EJNMMI Radiopharmacy and Chemistry 2016, 1:11, "New protein deposition tracers in the pipeline", and Ariza et al., J Med Chem 2015, 58(11), 4365-82: "Tau PET Imaging: Past, Present and Future". In addition, several patent applications have recently been published, e.g: WO 2013/176698, WO 2009/102498, WO 2011/119565, U.S. Pat. No. 8,932,557 B2 and U.S. Pat. No. 8,691,187, B2 (Siemens Medical Solutions, Lilly), WO 2012/067863 and WO 2012/068072 (both GE Healthcare) WO 2014/026881, WO 2014/177458, WO 2014/187762, WO 2015/044095, WO 2015/052105, WO 2015/173225 (Hoffmann-La Roche AG), WO 2015/188368 (Merck Sharp & Dohme) and WO 2016/124508 (UCB Biopharma SPRL) which claim novel compounds for Tau imaging.

In order to achieve high target selectivity, molecular probes have been used which recognize and bind to the pathological target. Selectivity for binding to pathological Tau protein over other protein depositions in the brain is therefore a basic requirement of a Tau imaging probe. In order to reduce background signal interference resulting from non-specific off-target binding (e.g. binding to Aβ or monoamine oxidases), imaging compounds should bind with high affinity to pathological Tau. Since amyloid or amyloid-like deposits formed from proteins of diverse primary amino acid sequences share a common β-sheet quaternary conformation, molecular probes are required that can differentiate such structures in order to avoid detection of other pathologies (false-positives) and therefore misdiagnosis.

Off-target binding to monoamine oxidase A or B have been reported to be a significant limitation for Tau tracers, especially T-807 and THK-5351 (Vermeiren, C, et al. Alzheimers & Dementia. 2015; 11 (7) Supplement p 1-2: "T807, a reported selective tau tracer, binds with nanomolar affinity to monoamine oxidase A"; Ng, K P, et al. Alzheimer's Research and Therapy 2017, 9:25: "Monoamine oxidase B inhibitor, selegiline, reduces $^{18}$F-THK5351 uptake in the human brain"). Off-target binding to monoamine oxidases A or B confound the interpretation of PET images with T807 and THK5351 with respect to tau. Presence of monoamine oxidases within several brain regions limits the interpretation of PET imaging results with these tracers.

Beside high selectivity, also binding to different Tau isoforms is an important aspect for a tau tracer. Up till now, most tracers show binding to tau in AD. However, tau in AD is a mixture of two isoforms, so called 3R-tau and 4R-tau. Other non-AD tauopathies are characterized by the predominant presence of one of these isoforms. In Pick's disease (PiD), the 3R tau isoform is predominantly present whereas in progressive supranuclear palsy (PSP) and in corticobasal degeneration (CBD), the 4R-tau isoform is the existing pathology.

In addition, molecular probes must also be designed such that upon administration they can distribute within the body and reach their target. For imaging of Tau aggregates associated with neurological disorders such as e.g. Alzheimer's disease, imaging compounds are required that can penetrate the blood brain barrier and pass into the relevant regions of the brain. For targeting intracellular Tau aggregates, cell permeability is an additional requirement of imaging compounds. A further prerequisite in order to get a sufficient signal-to-noise ratio is a fast compound wash-out from non-target regions in the brain (or other targeting organ). Also, compounds should show no defluorination, as bone uptake in the skull (as result from presence of free fluoride) will cause significant spill-over into the brain which limits the usability (Chien D T, et al. J Alzheimers Dis. 2014; 38:171-84).

The specifically disclosed and most advanced derivative of 2013/176698 is 2,5-disubstituted pyridine compound $^{18}$F-1 (also see U.S. Pat. No. 8,932,557 B2).

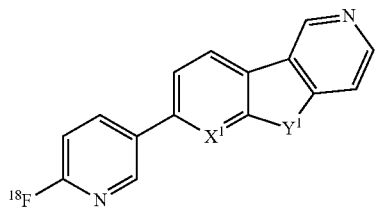

$X^1 = CH$
$Y^1 = NH$

Compound $^{18}$F-1 was investigated in various clinical studies. Although $^{18}$F-1 seems to be able to detect Tau in patients with AD or amyloid-beta positive mild cognitive impairment (MCI), various limitations have been reported.

Vermeiren and coworkers found that compound $^{18}$F-1 bound to Monoamine oxidase A (MAO A) with a $K_D$ of 1.5 nM. Their data unanimously demonstrate that compound $^{18}$F-1 binds to Tau aggregates and MAO-A with similar high affinity. The findings raise caution to the interpretation of compound $^{18}$F-1 clinical data, as MAO-A is widely expressed in most human brain regions (Vermeiren et al., Alzheimers & Dementia. 2015; 11 (7) Supplement p 1-2: T807-a reported selective Tau tracer, binds with nanomolar affinity to Monoamine oxidase A).

Compound $^{18}$F-1 was reported to have a fairly strong signal in parts of the brain's basal ganglia, e.g., the striatum and substantia nigra, regardless of the patient's diagnosis. The signal of $^{18}$F-1 in the cortex did not reach a "steady state" (a window of time during which the ratio of binding in a target region to binding in the reference tissue (i.e. cerebellum) was stable). In addition, the kinetics of $^{18}$F-1 in various brain regions was different and never stabilized in a 150-minute scanning period (S. Baker, Human Amyloid Imaging Meeting, 2015).

Binding of compound $^{18}$F-1 to AD brain sections was demonstrated by autoradiography. However, compound $^{18}$F-1 showed limitations in binding to brain sections with pathologies of non-AD tauopathies a) Lowe V J, et al. An autoradiographic evaluation of AV-1451 Tau PET in dementia. *Acta Neuropathologica Communications*. 2016; 4:58; b) Marquie M, et al. Validating novel Tau Positron Emission Tomography Tracer [F-18]-AV-1451 (T807) on postmortem Brain Tissue. *Annals of Neurology*. 2015; 78:787; c) Gomez F, et al. Quantitative assessment of [$^{18}$F]AV-1451 distribution in AD, PSP and PiD Post-Mortem Brain Tissue Sections relative to that of the anti-Tau antibody ATB. *Journal of Nuclear Medicine*. 2016; 57, S2: 348, d) Sander K, et al. Characterization of tau positron emission tomography tracer AV1451 binding to postmortem tissue in Alzheimer's disease, primary tauopathies, and other dementias. *Alzheimers Dementia* 2016, 12(11): 116-1124 e) Smith R, et al. Increased basal ganglia binding of 18F-AV-1451 in patients with progressive supranuclear palsy. *Movement disorders* 2016.

Also clinically, $^{18}$F-1 seem to be of limited value for the detection of tau in PSP subjects a) Smith R et al., Tau neuropathology correlates with FDG-PET, but nor with AV-1451-PET, in progressive supranuclear palsy. Acta Neuropathologica 2017, 133:149-151; b) Smith R, et al. Increased basal ganglia binding of 18F-AV-1451 in patients with progressive supranuclear palsy. *Movement disorders* 2017, 32(1), 108-114.

The final conclusions from these studies indicate that T807/AV1451 might not reliable to distinguish individual patients with PSP from controls. This is mainly attributed to an increased unspecific binding in midbrain structures like basal ganglia. Uptake seen in cerebral cortex and white matter did not reflected tau pathology in PSP.

Compound $^{18}$F-2 is disclosed in WO 2015/052105.

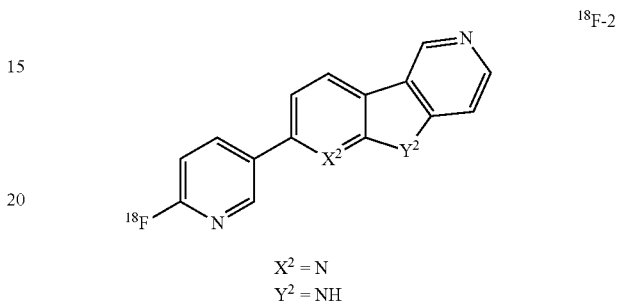

$X^2 = N$
$Y^2 = NH$

WO 2015/052105 only discloses one $^{18}$F-labeled compound and a corresponding compound which is tritium labeled. The compound comprises a 2,5-disubstituted pyridine moiety (compound $^{18}$F-2). WO 2015/052105 does not provide any data on binding to Tau-isoforms in non-AD tauopathies, binding to MAO A (or otherwise on selectivity to Tau), brain uptake, brain washout or retention in healthy brain, or any data on in vivo de-fluorination.

$^{18}$F-2 was found to not bind to brain tissue from patients with non-AD tauopathies such as Pick's disease (PiD) and progressive supranuclear palsy (PSP) (Honer M et al., In vitro binding of $^3$H-RO6958948, $^3$H-AV-1451, $^3$H-THK5351 and $^3$H-T808 to tau aggregates in non-AD tauopathies. Human Amyloid Imaging 2017, abstract 99).

In view of the above mentioned prior art, it was an object of the present invention to provide a compound which has a high affinity and selectivity for Tau and is thus suitable as a PET imaging agent. Preferably, the compounds of the present invention demonstrate high affinity to Tau aggregates, high selectivity towards pathological Tau compared to other targets in the brain and favorable pharmacokinetic properties without defluorination.

SUMMARY OF THE INVENTION

Therefore, the present invention relates to the following items:
1. A compound of the formula (I)

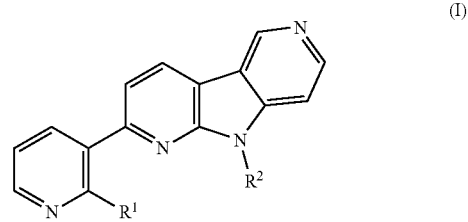

as well as pharmaceutically acceptable salts, hydrates, solvates, prodrugs and polymorphs thereof;

wherein
R$^1$ is selected from the group consisting of $^{18}$F, F and LG;
R$^2$ is H or PG;
PG is a protecting group;
LG is a leaving group.
2. The compound according to item 1, wherein R$^1$ is $^{18}$F and R$^2$ is H.
3. The compound according to item 1, wherein R$^1$ is F and R$^2$ is H.
4. The compound according to item 1, wherein R$^1$ is LG and R$^2$ is H or PG.
5. The compound according to item 1 or 4, wherein R$^1$ is LG and R$^2$ is H.
6. The compound according to item 1 or 4, wherein R$^1$ is LG and R$^2$ is PG.
7. The compound according to item 1, 4, 5 or 6, wherein LG is nitro, halogen or trimethyl ammonium.
8. The compound according to item 7, wherein LG is nitro or trimethyl ammonium.
9. The compound according to item 1, 4, 6, 7, or 8, wherein PG is tert-butyloxycarbonyl (BOC), triphenylmethyl (Trityl) or dimethoxytrityl (DMT).
10. The compound according to item 9, wherein PG is tert-butyloxycarbonyl (BOC).
11. The compound according to item 1, wherein the compound is detectably labeled.
12. The compound according to item 11, wherein the detectable label is selected from $^2$H, $^3$H and $^{18}$F.
13. The compound according to item 12, wherein the detectable label is $^{18}$F.
14. A diagnostic composition comprising a compound as defined in any of items 2, 11, 12 or 13 and optionally a pharmaceutically acceptable carrier, diluent, adjuvant or excipient.
15. A compound as defined in item 2 or 13 for use in diagnostics.
16. A compound as defined in item 2 or 13 for use in the imaging of Tau aggregates, particularly for use in positron emission tomography imaging of Tau aggregates.
17. A compound as defined in item 2 or 13 for use in the diagnosis of a disorder associated with Tau aggregates or for use in the diagnosis of a tauopathy, particularly wherein the diagnosis is conducted by positron emission tomography.
18. A compound for use according to item 17, wherein the tauopathy is a 3R tauopathy.
19. A compound for use according to item 17, wherein the tauopathy is a 4R tauopathy.
20. The compound for use according to item 17, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury (TBI), amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy; preferably Alzheimer's disease.
21. The compound for use according to item 20, wherein the disorder is Alzheimer's disease (AD).
22. The compound for use according to item 20, wherein the disorder is Parkinson's disease or atypical parkinsonism.
23. The compound for use according to item 20, wherein the disorder is progressive supranuclear palsy (PSP).
24. The compound for use according to item 20, wherein the disorder is Pick's disease (PiD).
25. The compound for use according to any one of items 16 to 24, wherein the Tau aggregates are imaged in the brain or in the eye, preferably wherein the detectable label is $^{18}$F and the imaging is positron emission tomography.
26. A method of imaging of Tau aggregates, particularly a method of positron emission tomography imaging of Tau aggregates, wherein an effective amount of a compound as defined in item 2 or 13 is administered to a patient.
27. A method of diagnosing a disorder associated with Tau aggregates or a tauopathy, wherein an effective amount of a compound as defined in item 2 or 13 is administered to a patient, particularly wherein the diagnosis is conducted by positron emission tomography.
28. A method according to item 27, wherein the tauopathy is a 3R tauopathy.
29. A method according to item 27, wherein the tauopathy is a 4R tauopathy.
30. The method according to item 27, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy; preferably Alzheimer's disease.

31. The method according to item 30, wherein the disorder is Alzheimer's disease (AD).
32. The method according to item 30, wherein the disorder is Parkinson's disease or atypical parkinsonism.
33. The method according to item 30, wherein the disorder is progressive supranuclear palsy (PSP).
34. The method according to item 30, wherein the disorder is Pick's disease (PiD).
35. The method according to any one of items 26 to 34, wherein the Tau aggregates are imaged in the brain or in the eye, preferably wherein the detectable label is $^{18}$F and the imaging is positron emission tomography.
36. Use of a compound as defined in item 2 or 13 for the manufacture of a diagnostic agent for imaging of Tau aggregates, particularly for positron emission tomography imaging of Tau aggregates.
37. Use of a compound as defined in item 2 or 13 for the manufacture of a diagnostic agent for diagnosing a disorder associated with Tau aggregates or for diagnosing a tauopathy, particularly wherein the diagnosis is conducted by positron emission tomography.
38. The use according to item 37, wherein the tauopathy is a 3R tauopathy.
39. The use according to item 37, wherein the tauopathy is a 4R tauopathy.
40. The use according to item 37, wherein the disorder is selected from Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy; preferably Alzheimer's disease.
41. The use according to item 40, wherein the disorder is Alzheimer's disease (AD).
42. The use according to item 40, wherein the disorder is Parkinson's disease or atypical parkinsonism.
43. The use according to item 40, wherein the disorder is progressive supranuclear palsy (PSP).
44. The use according to item 40, wherein the disorder is Pick's disease (PiD).
45. The use according to any one of items 36 to 44, wherein the Tau aggregates are imaged in the brain or in the eye, preferably wherein the detectable label is $^{18}$F and the imaging is positron emission tomography.
46. Use of the compound according to item 3 as an analytical reference.
47. Use of the compound according to item 3 as an in vitro screening tool.
48. A method of preparing a compound as defined in item 2 comprising reacting a compound as defined in item 4 with a [$^{18}$F]fluorinating agent, wherein the method further comprises cleaving of the protecting group PG, if present.
49. The method according to item 48, wherein the [$^{18}$F] fluorinating agent is selected from K$^{18}$F, H$^{18}$F, Cs$^{18}$F, Na$^{18}$F and a tetra(C$_{1-6}$ alkyl) ammonium salt of $^{18}$F.
50. A method of preparing a diagnostic composition as defined in item 14 comprising reacting a compound as defined in item 4 with a [$^{18}$F]fluorinating agent, wherein the method further comprises cleaving of the protecting group PG, if present, and subsequently optionally admixing a pharmaceutically acceptable carrier, diluent, adjuvant or excipient.
51. A kit for preparing a radiopharmaceutical preparation, said kit comprising a sealed vial containing a predetermined quantity of a compound as defined in item 4.
52. The kit according to item 51, which further comprises at least one component selected from a reaction solvent, a solid-phase extraction cartridge, a reagent for cleaving the protecting group, a solvent for purification, a solvent for formulation and a pharmaceutically acceptable carrier, diluent, adjuvant or excipient for formulation.
53. A method of collecting data for the diagnosis of a disorder associated with tau aggregates in a sample or a patient comprising:
    (a) bringing a sample or a specific body part or body area suspected to contain a tau aggregate into contact with a compound as defined in items 11 to 13;
    (b) allowing the compound to bind to the tau aggregate;
    (c) detecting the compound bound to the tau aggregate; and
    (d) optionally correlating the presence or absence of compound binding with the tau aggregate with the presence or absence of tau aggregate in the sample or specific body part or body area.
54. A method of determining the amount of tau aggregate in a tissue and/or a body fluid comprising:
    (a) providing a sample representative of the tissue and/or body fluid under investigation;
    (b) testing the sample for the presence of tau aggregate with a compound as defined in items 11 to 13;
    (c) determining the amount of compound bound to the tau aggregate; and
    (d) calculating the amount of tau aggregate in the tissue and/or body fluid.
55. A method of collecting data for determining a predisposition to a disorder associated with tau aggregates in a patient comprising detecting the specific binding of a compound as defined in items 11 to 13 to a tau aggregate in a sample or in situ which comprises the steps of:
(a) bringing the sample or a specific body part or body area suspected to contain the tau aggregate into contact with the compound as defined in items 11 to 13, which compound specifically binds to the tau aggregate;
(b) allowing the compound to bind to the tau aggregate to form a compound/tau aggregate complex;
(c) detecting the formation of the compound/tau aggregate complex;
(d) optionally correlating the presence or absence of the compound/tau aggregate complex with the presence or absence of tau aggregate in the sample or specific body part or body area; and
(e) optionally comparing the amount of the compound/tau aggregate to a normal control value.

56. A method of collecting data for monitoring residual disorder in a patient suffering from a disorder associated with tau aggregates who has been treated with a medicament, wherein the method comprises:
(a) bringing a sample or a specific body part or body area suspected to contain a tau aggregate into contact with a compound as defined in items 11 to 13, which compound specifically binds to the tau aggregate;
(b) allowing the compound to bind to the tau aggregate to form a compound/tau aggregate complex;
(c) detecting the formation of the compound/tau aggregate complex;
(d) optionally correlating the presence or absence of the compound/tau aggregate complex with the presence or absence of tau aggregate in the sample or specific body part or body area; and
(e) optionally comparing the amount of the compound/tau aggregate to a normal control value.

57. A method of collecting data for predicting responsiveness of a patient suffering from a disorder associated with tau aggregates and being treated with a medicament comprising:
(a) bringing a sample or a specific body part or body area suspected to contain an tau aggregate into contact with a compound as defined in items 11 to 13, which compound specifically binds to the tau aggregate;
(b) allowing the compound to bind to the tau aggregate to form a compound/tau aggregate complex;
(c) detecting the formation of the compound/tau aggregate complex;
(d) optionally correlating the presence or absence of the compound/tau aggregate complex with the presence or absence of tau aggregate in the sample or specific body part or body area; and
(e) optionally comparing the amount of the compound/tau aggregate to a normal control value.

It is understood that the present invention covers compounds of the formula (I) in which one or more of the respective atoms is replaced by a different isotope. For instance, the compounds of the formula (I) include compounds in which one or more of the hydrogen atoms is replaced by tritium and/or one or more of the hydrogen atoms is replaced by deuterium.

The present inventors have surprisingly found that the compounds of the formula (I) in which $R^1$ is $^{18}F$ or F and $R^2$ is H (compounds F-4 and $^{18}F$-4, respectively) have significantly improved properties compared to the prior art compounds $^{18}F$-1 or $^{18}F$-2.

DETAILED DESCRIPTION

Figure 1:
FIG. 1: Autoradiography of AD and HC brain slices with compound $^{18}F$-4. In the AD brain sections, a strong punctated staining was detectable that could be blocked with the addition of excess corresponding cold compound. In the healthy control (HC) sections, no specific signal was visible.

The present invention relates to detectably labeled compounds of the formula (I)

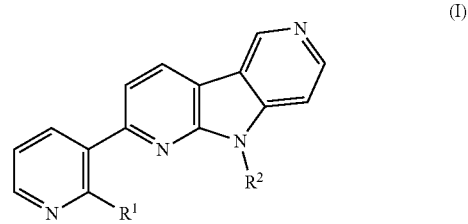

(I)

that can be employed in the selective detection of disorders and abnormalities associated with Tau aggregates such as Alzheimer's disease and other tauopathies, for example, by using Positron Emission Tomography (PET) imaging. The present invention also refers to intermediates which can be used in the production of such imaging compounds. The present compounds have a high affinity for Tau and bind to Tau-isoforms present in both, Alzheimer's disease (AD), as well as in non-AD tauopathies, such as for example progressive supranuclear palsy (PSP), and Pick's disease (PiD). Since they have a low affinity for amyloid-beta and MAO A they can be used as highly selective molecular probes for binding pathological Tau and thus avoid detection of other pathologies and misdiagnosis.

The instant $^{18}F$-labeled compounds also lead to a low signal in healthy brain, so that they can reduce background signal interference and thus provide a low detection limit.

Due to their good brain uptake, fast washout from healthy brain, low long-term retention in healthy brain as well as the lack of in vivo de-fluorination the instant compounds provide a good signal-to-noise ratio.

Furthermore, the instant compounds can be easily detectably labeled, e.g., with $^{18}F$, in high yields.

Definitions

The term "protecting group" (PG) as employed herein is any protecting group which is suitable for protecting an amine group during an envisaged chemical reaction. Examples of suitable protecting groups are well-known to a person skilled in the art. Suitable protecting groups are discussed, e.g., in the textbook Greene and Wuts, Protecting groups in Organic Synthesis, third edition, page 494-653, which is included herein by reference. Protecting groups can be chosen from carbamates, amides, imides, N-alkyl amines, N-aryl amines, imines, enamines, boranes, N—P protecting groups, N-sulfenyl, N-sulfonyl and N-silyl. Specific preferred examples of protecting groups (PG) are carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT), or dimethoxytrityl (DMT). More preferred examples of the protecting group PG include tert-butyloxycarbonyl (BOC), dimethoxytrityl (DMT) and triphenylmethyl (Trityl). One more preferred example of the protecting group PG is tert-butyloxycarbonyl (BOC).

The term "leaving group" (LG) as employed herein is any leaving group and means an atom or group of atoms can be replaced by another atom or group of atoms. Examples are given e.g. in Synthesis (1982), p. 85-125, table 2, Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33). Preferably, the "leaving group" (LG) is nitro, halogen or trimethyl ammonium. More preferably, "leaving group" (LG) is nitro or trimethyl ammonium. In one preferred embodiment, "leaving group" (LG) is nitro. In another preferred embodiment, "leaving group" (LG) is trimethyl ammonium.

Tau as used herein refers to a highly soluble microtubule binding protein mostly found in neurons and includes the major 6 isoforms, cleaved or truncated forms, and other modified forms such as arising from phosphorylation, glycosylation, glycation, prolyl isomerization, nitration, acetylation, polyamination, ubiquitination, sumoylation and oxidation. Pathologic Tau or Tau aggregates (Neurofibrillary Tangles, NFTs) as used herein refer to insoluble aggregates of the hyperphosphorylated Tau protein containing paired helical filaments and straight filaments. Their presence is a hallmark of AD and other diseases known as tauopathies.

The term "polymorphs" refers to the various crystalline structures of the compounds of the present invention. This may include, but is not limited to, crystal morphologies (and amorphous materials) and all crystal lattice forms. Salts of the present invention can be crystalline and may exist as more than one polymorph.

Solvates, hydrates as well as anhydrous forms of the present compounds are also encompassed by the invention. The solvent included in the solvates is not particularly limited and can be any pharmaceutically acceptable solvent. Examples include water and $C_{1-4}$ alcohols (such as methanol or ethanol).

As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

As used hereinafter in the description of the invention and in the claims, the term "pharmaceutically acceptable salt" relates to non-toxic derivatives of the disclosed compounds wherein the parent compound is modified by making salts of inorganic and organic acids thereof. Inorganic acids include, but are not limited to, acids such as carboxylic, hydrochloric, nitric or sulfuric acid. Organic acids include, but are not limited to, acids such as aliphatic, cycloaliphatic, aromatic, araliphatic, heterocyclic, carboxylic and sulphonic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts can be found in Remington's Pharmaceutical Sciences, 18th ed., Mack Publishing Company, Easton, Pa., 1990, p. 1445, the disclosure of which is hereby incorporated by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The patients or subjects in the present invention are typically animals, particularly mammals, more particularly humans.

The tau gene contains 16 exons with the major tau protein isoforms being encoded by 11 of them The alternative splicing of exon 10 generates tau isoforms with either three (exon 10 missing) or four (exon 10 present) repeat domains, known as 3R and 4R tau, respectively (A. Andreadis et al., Biochemistry 31, (1992) 10626-10633; M. Tolnay et al., IUBMB Life, 55(6): 299-305, 2003). In Alzheimer's disease, the ratio of 3R and 4R isoforms is similar. In contrast thereto, in some tauopathies one of the two isoforms is predominantly present. Herein, the term "3R tauopathy" refers to tauopathies (such as Pick's disease (PiD)) in which the 3R isoform is predominantly present. Herein, the term "4R tauopathy" refers to tauopathies (such as progressive supranuclear palsy (PSP) and corticobasal degeneration (CBD)) in which the 4R isoform is predominantly present.

The preferred definitions given in the "Definition"-section apply to all of the embodiments described herein unless stated otherwise.

Diagnostic Procedures

The detectably labeled compounds of the present invention (in particular $^{18}$F-4) are particularly suitable for imaging of Tau protein aggregates. With respect to Tau protein, the detectably labeled compounds of the present invention (in particular $^{18}$F-4) are able to bind to various types of Tau aggregates such as pathologically aggregated Tau, hyperphosphorylated Tau, neurofibrillary tangles, paired helical filaments, straight filaments, neurotoxic soluble oligomers, polymers and fibrils.

Due to the above binding characteristics, the detectably labeled compounds of the present invention (in particular $^{18}$F-4) are suitable for use in the diagnosis of disorders associated with Tau aggregates. The detectably labeled compounds of the present invention (in particular $^{18}$F-4) are particularly suitable for positron emission tomography (PET) imaging of Tau deposits. Typically $^{18}$F labeled compounds of the formula (I) are employed as detectably labeled compounds if the compounds are to be administered to a patient.

In the imaging of Tau aggregates a detectably labeled compound of the formula (I) (preferably $^{18}$F-4) is administered and the signal stemming from the compound that is specifically bound to the Tau aggregates is detected. The specific binding is a result of the high binding affinity of the compounds of the formula (I) to the Tau aggregates.

In a preferred embodiment, a detectably labeled compound of the formula (I) (preferably $^{18}$F-4) is employed for diagnosing whether a tauopathy (preferably Alzheimer's disease) is present. In this method a detectably labeled compound of the formula (I) (preferably $^{18}$F-4) is administered to a patient who is suspected to suffer from a tauopathy (preferably Alzheimer's disease) or a sample obtained from such a patient and the signal stemming from the detectable label is detected, preferably by positron emission tomography (PET).

If no signal stemming from the detectable label is detected then the instant method can be used to exclude a tauopathy, which indicates that a neurological disorder other than a tauopathy is present.

In the methods of diagnosing a disorder associated with Tau protein aggregates such as Alzheimer's disease, or a predisposition therefor in a subject, the method comprising:
a) administering to the mammal a diagnostically effective amount of a detectably labeled compound of the present invention (in particular $^{18}$F-4);
b) allowing the detectably labeled compound of the present invention (in particular $^{18}$F-4) to distribute into the tissue of interest (such as brain tissue, the eye or body fluids such as cerebrospinal fluid (CSF)); and
c) imaging the tissue of interest, wherein an increase in binding of the detectably labeled compound of the present invention (in particular $^{18}$F-4) to the tissue of interest compared to a normal control level of binding indicates that the subject is suffering from or is at risk of developing a disorder associated with Tau protein aggregates.

The detectably labeled compounds of the present invention (in particular $^{18}$F-4) can be used for imaging of Tau protein aggregates in any sample or a specific body part or body area of a patient which suspected to contain a Tau protein aggregate. The detectably labeled compounds of the present invention (in particular $^{18}$F-4) are able to pass the blood-brain barrier and to pass into the eye. Consequently, they are particularly suitable for imaging of Tau protein aggregates in the brain, in the eye (ophthalmic and/or retinal imaging) as well as in body fluids such as cerebrospinal fluid (CSF).

In diagnostic applications, the detectably labeled compounds of the present invention (in particular $^{18}$F-4) are preferably administered in a diagnostic composition.

Diagnosis of a Tau disorder or of a predisposition to a Tau-associated disorder in a patient may be achieved by detecting the specific binding of a detectably labeled compound of the present invention (in particular $^{18}$F-4) to the Tau protein aggregates in a sample or in situ, which includes:
(a) bringing the sample or a specific body part or body area suspected to contain the Tau protein aggregate into contact with a detectably labeled compound of the present invention (in particular $^{18}$F-4) which binds the Tau protein aggregate;
(b) allowing the detectably labeled compound of the present invention (in particular $^{18}$F-4) to bind to the Tau protein aggregate to form a compound/Tau protein aggregate complex (hereinafter "compound/Tau protein aggregate complex" will be abbreviated as "compound/protein aggregate complex");
(c) detecting the formation of the compound/protein complex,
(d) optionally correlating the presence or absence of the compound/protein complex with the presence or absence of Tau protein aggregates in the sample or specific body part or area; and
(e) optionally comparing the amount of the compound/protein to a normal control value, wherein an increase in the amount of the compound/protein compared to a normal control value may indicate that the patient is suffering from or is at risk of developing a Tau-associated disorder.

After the sample or a specific body part or body area has been brought into contact with the detectably labeled compound of the present invention (in particular $^{18}$F-4), the compound is allowed to bind to the Tau protein aggregate. The amount of time required for binding will depend on the type of test (e.g., in vitro or in vivo) and can be determined by a person skilled in the field by routine experiments.

The compound which has bound to the Tau protein aggregate can be subsequently detected by any appropriate method. A preferred method is positron emission tomography (PET).

The presence or absence of the compound/protein is then optionally correlated with the presence or absence of Tau protein aggregates in the sample or specific body part or area. Finally, the amount of the compound/protein can be compared to a normal control value which has been determined in a sample or a specific body part or body area of a healthy subject, wherein an increase in the amount of the compound/protein compared to a normal control value may indicate that the patient is suffering from or is at risk of developing a Tau-associated disorder.

The present invention also relates to a method of determining the amount of Tau protein aggregate in a tissue and/or a body fluid. This method comprises the steps of:
(a) providing a sample representative of the tissue and/or body fluid under investigation;
(b) testing the sample for the presence of Tau protein aggregate with a detectably labeled compound of the present invention (in particular $^{18}$F-4);
(c) determining the amount of the detectably labeled compound of the present invention (in particular $^{18}$F-4) bound to the Tau protein aggregate; and
(d) calculating the amount of Tau protein aggregate in the tissue and/or body fluid.

The sample can be tested for the presence of Tau protein aggregate with a detectably labeled compound of the present invention (in particular $^{18}$F-4) by bringing the sample into contact with a detectably labeled compound of the present invention (in particular $^{18}$F-4), allowing the detectably labeled compound of the present invention (in particular $^{18}$F-4) to bind to the Tau protein aggregate to form a compound/protein aggregate complex and detecting the formation of the compound/protein complex as explained above.

Monitoring minimal residual disorder in a patient suffering from a disorder associated with Tau protein aggregates who has been treated with a medicament with a detectably labeled compound of the present invention (in particular $^{18}$F-4) may be achieved by:
(a) bringing a sample or a specific body part or body area suspected to contain a Tau protein aggregate into contact with a detectably labeled compound of the present invention (in particular $^{18}$F-4);
(b) allowing the detectably labeled compound of the present invention (in particular $^{18}$F-4) to bind to the Tau protein aggregate to form a compound/protein aggregate complex;
(c) detecting the formation of the compound/protein aggregate complex;
(d) optionally correlating the presence or absence of the compound/protein aggregate complex with the presence or absence of Tau protein aggregate in the sample or specific body part or body area; and
(e) optionally comparing the amount of the compound/protein aggregate to a normal control value, wherein an increase in the amount of the aggregate compared to a normal control value may indicate that the patient may still suffer from a minimal residual disease.

How steps (a) to (e) can be conducted has already been explained above.

Predicting responsiveness of a patient suffering from a disorder associated with Tau protein aggregates and being treated with a medicament can be achieved by (a) bringing a sample or a specific body part or body area suspected to contain a Tau protein aggregate into contact with a detectably labeled compound of the present invention (in particular $^{18}$F-4);
(b) allowing the detectably labeled compound of the present invention (in particular $^{18}$F-4) to bind to the Tau protein aggregate to form a compound/protein aggregate complex;
(c) detecting the formation of the compound/protein aggregate complex;
(d) optionally correlating the presence or absence of the compound/protein aggregate complex with the presence or absence of Tau protein aggregate in the sample or specific body part or body area; and
(e) optionally comparing the amount of the compound/protein aggregate to a normal control value.

How steps (a) to (e) can be conducted has already been explained above.

In the method for predicting responsiveness the amount of the compound/protein complex can be optionally compared at various points of time during the treatment, for instance, before and after onset of the treatment or at various points of time after the onset of the treatment. A change, especially a decrease, in the amount of the compound/protein complex may indicate that the patient has a high potential of being responsive to the respective treatment.

A compound according to the present invention can also be incorporated into a test kit for detecting a Tau protein aggregate. The test kit typically comprises a container holding one or more compounds according to the present invention and instructions for using the compound for the purpose of binding to a Tau protein aggregate to form a compound/protein complex and detecting the formation of the compound/protein complex such that presence or absence of the compound/protein complex correlates with the presence or absence of the Tau protein aggregates.

The term "test kit" refers in general to any diagnostic kit known in the art. More specifically, the latter term refers to a diagnostic kit as described in Zrein et al., Clin. Diagn. Lab. Immunol., 1998, 5, 45-49.

Diagnostic Compositions

A "diagnostic composition" is defined in the present invention as a composition comprising a detectably labeled compound of the present invention (preferably $^{18}$F labeled; in particular $^{18}$F-4). For in vivo applications the diagnostic composition should be in a form suitable for administration to mammals such as humans. Preferably a diagnostic composition further comprises a physiologically acceptable carrier, diluent, adjuvant or excipient. Administration to a patient is preferably carried out by injection of the composition as an aqueous solution. Such a composition may optionally contain further ingredients such as solvents, buffers; pharmaceutically acceptable solubilizers; and pharmaceutically acceptable stabilizers or antioxidants.

Pharmaceutically acceptable excipients are well known in the pharmaceutical art, and are described, for example, in Remington's Pharmaceutical Sciences, 15$^{th}$ Ed., Mack Publishing Co., New Jersey (1975). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the diagnostic composition of the present invention may comprise, for example, carriers, vehicles, diluents, solvents and edible oils, oily esters, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers.

If the detectably labeled compounds of the present invention (preferably $^{18}$F labeled, in particular $^{18}$F-4) are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other excipients. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The dose of the detectably labeled compounds of the present invention (preferably $^{18}$F labeled, in particular $^{18}$F-4) will vary depending on the exact compound to be administered, the weight of the patient, size and type of the sample, and other variables as would be apparent to a physician skilled in the art. Generally, the dose could preferably lie in the range 0.001 µg/kg to 10 µg/kg, preferably 0.01 µg/kg to 1.0 µg/kg. The radioactive dose can be, e.g., 100 to 600 MBq, more preferably 150 to 450 MBq.

The diagnostic compositions of the invention can be produced in a manner known per se to the skilled person as described, for example, in Remington's Pharmaceutical Sciences, 15$^{th}$ Ed., Mack Publishing Co., New Jersey (1975).

For instance, the compounds of the present invention can be employed in a liposomal composition as described in WO2016057812A1 which comprises a compound of formula (II) as a ligand for use in the selective detection of disorders and abnormalities associated with Tau aggregates by nonradioactive magnetic resonance imaging (MRI).

In particular, in one embodiment diseases or disorders that can be detected and monitored with the detectably labeled compounds of the present invention (in particular $^{18}$F-4) are diseases or conditions associated Tau proteins aggregates.

The diseases or conditions that can be detected and monitored with the detectably labeled compounds of the present invention (in particular $^{18}$F-4) include neurodegenerative disorders such as tauopathies. Examples of diseases and conditions which can be detected and monitored are caused by or associated with the formation of neurofibrillary lesions. This is the predominant brain pathology in tauopathy. The diseases and conditions comprise a heterogeneous group of neurodegenerative diseases or conditions including diseases or conditions which show co-existence of Tau and amyloid pathologies. Examples of diseases involving Tau aggregates are generally listed as tauopathies and these include, but are not limited to, Alzheimer's disease (AD), Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration (such as age-related macular degeneration (AMD)), optic nerve drusen, optic neuropathy, optic neuritis, and lattice dystrophy. Preferably the diseases and conditions which can be detected and monitored include Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury (TBI), amyotrophic lateral sclerosis, Parkinsonism-dementia complex of Guam, non-Guamanian motor neuron disease with neurofibrillary tangles, argyrophilic grain disease, corticobasal degeneration (CBD), diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease (PiD), progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, and white matter tauopathy with globular glial inclusions, more preferably Alzheimer's disease (AD), Creutzfeldt-Jacob disease, dementia pugilistica, amyotrophic lateral sclerosis, argyrophilic grain disease, corticobasal degeneration, frontotemporal dementia with Parkinsonism linked to chromosome 17, Pick's disease, progressive supranuclear palsy (PSP), tangle only dementia, Parkinson dementia complex of Guam, Hallervorden-Spatz disease and fronto-temporal lobar degeneration. Preferably the disease or condition is Alzheimer's disease.

General Synthesis of $^{18}$F-Labeled Compounds of the Present Invention

Compounds having the formula (I) which are labeled by $^{18}$F can be prepared by reacting a compound of formula (I), in which $R^1$ is LG and $R^2$ is H or PG, with an $^{18}$F-fluorinating agent, so that the leaving group LG is replaced by $^{18}$F. The preparation includes the cleavage of the protecting group PG, if present.

Any suitable $^{18}$F-fluorinating agent can be employed. Typical examples include H$^{18}$F, alkali or alkaline earth $^{18}$F-fluorides (e.g., K$^{18}$F, Rb$^{18}$F, Cs$^{18}$F, and Na$^{18}$F). Optionally, the $^{18}$F-fluorination agent can be used in combination with a chelating agent such as a cryptand (e.g.: 4,7,13,16, 21,24-hexaoxa-1,10-diazabicyclo[8.8.8]-hexacosane—Kryptofix®) or a crown ether (e.g.: 18-crown-6). Alternatively, the $^{18}$F-fluorinating agent can be a tetraalkyl ammonium salt of $^{18}$F or a tetraalkyl phosphonium salt of $^{18}$F; e.g., tetra($C_{1-6}$ alkyl)ammonium salt of $^{18}$F or a tetra ($C_{1-6}$ alkyl)phosphonium salt of $^{18}$F. Examples thereof include tetrabutyl ammonium [$^{18}$F]fluoride and tetrabutyl phosphonium [$^{18}$F]fluoride. Preferably, the $^{18}$F-fluorination agent is K$^{18}$F, H$^{18}$F, Cs$^{18}$F, Na$^{18}$F or tetrabutyl ammonium [$^{18}$F]fluoride.

The reagents, solvents and conditions which can be used for the $^{18}$F-fluorination are well-known to a person skilled in the field (L. Cai, S. Lu, V. Pike, Eur. J. Org. Chem 2008, 2853-2873; J. Fluorine Chem., 27 (1985): 177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the $^{18}$F-fluorination are DMF, DMSO, acetonitrile, DMA, or mixtures thereof, preferably the solvent is acetonitrile or DMSO.

If desired, the compound having the formula (I) can have $R^1$ is LG and $R^2$ is PG, wherein the protecting group PG protects the amine during the $^{18}$F-fluorination reaction. This amine protecting group can be subsequently removed. Methods for removing the amine protecting group are known in the art and include, but are not limited to, acidic cleavage.

If desired, the compound of formula (I) can be isolated and/or purified further before use. Corresponding procedures are well-known in the art.

The precursor compounds having the formula (I) in which $R^1$ is LG and $R^2$ is H or PG can be provided in a kit which is suitable for producing the compounds of the formula (I) by reaction with a $^{18}$F-fluorinating agent. In one embodiment the kit comprises a sealed vial containing a predetermined quantity of the precursor compound of the present invention. For instance, the kit can contain 1.5 to 75 µmol, preferably 7.5 to 50 µmol, more preferably 10 to 30 µmol of a precursor compound (I) of the present invention. Optionally, the kit can contain further components, such as a reaction solvent, a solid-phase extraction cartridge, a reagent to obtain the $^{18}$F-fluorinating agent, a reagent for cleaving the protecting group, a solvent for purification, a solvent for formulation and a pharmaceutically acceptable carrier, diluent, adjuvant or excipient for formulation.

The compounds of the present invention in which $R^1$ is F and $R^2$ is H can be used as an analytical reference or an in vitro screening tool.

The compounds of the present invention in which $R^1$ is F and $R^2$ is H can be used as an analytical reference for the quality control and release of a compound of the present invention in which $R^1$ is $^{18}$F and $R^2$ is H.

The compounds of the present invention in which $R^1$ is F and $R^2$ is H can be used as an in vitro screening tool for characterization of tissue with Tau pathology and for testing of compounds targeting Tau pathology on such tissue.

The present invention illustrated by the following examples which should not be construed as limiting.

EXAMPLES

All reagents and solvents were obtained from commercial sources and used without further purification. Proton ($^1$H) spectra were recorded on a Bruker DRX-400 MHz NMR spectrometer or on a Bruker AV-400 MHz NMR spectrometer in deuterated solvents. Mass spectra (MS) were recorded on an Advion CMS mass spectrometer. Chromatography was performed using silica gel (Fluka: Silica gel 60, 0.063-0.2 mm) and suitable solvents as indicated in the specific examples. Flash purification was conducted with a Biotage Isolera One flash purification system using HP-Sil (Biotage) or puriFlash-columns (Interchim) and the solvent gradient indicated in the specific examples. Thin layer chromatography (TLC) was carried out on silica gel plates with UV detection.

Although some of the present examples do not indicate that the respective compounds were detectably labeled, it is understood that corresponding detectably labeled compounds can be easily prepared, e.g., by using detectably labeled starting materials, such as starting materials containing $^3$H atoms.

ABBREVIATIONS

| | |
|---|---|
| AD | Alzheimer's disease |
| Boc, BOC | tert-butyloxycarbonyl |
| CBD | corticobasal degeneration |
| d.c. | corrected for decay |
| d | doublet |
| dd | doublet of doublet |
| ddd | doublet of doublet of doublet |
| dt | doublet of triplet |
| DMF | N,N-dimethyl formamide |
| DMSO | dimethylsulfoxide |
| EI | electron ionisation |
| ELSD | evaporative light scattering detector |
| ESI | electrospray ionisation |
| FTD | Frontotemporal dementia |
| HPLC | high performance liquid chromatography |
| HC | Healthy control |
| GBq | Gigabequerel |
| $K_{222}$ | 4,7,13,16,21,24-hexaoxa-1,10-diazabicyclo[8.8.8]-hexacosane (Kryptofix 222) |
| MBq | Megabequerel |
| MS | mass spectrometry |
| MeCN | acetonitrile |
| m | multiplet |
| mc | centered multiplet |
| n.c.a. | non-carrier-added |
| n.d.c. | not decay corrected |
| NMR | nuclear magnetic resonance spectroscopy: chemical shifts (δ) are given in ppm. |
| PET | Positron-Emission-Tomography |
| PiD | Pick's disease |
| PSP | progressive supranuclear palsy |
| q | quadruplet (quartet) |
| RT | room temperature |
| s | singulet |
| t | triplet |
| Tau | Tau protein, Tau deposits, Tau aggregates |
| TBI | Traumatic brain injury |
| Trt | trityl (triphenylmethyl) |
| TLC | thin layer chromatography |

Preparative Example A

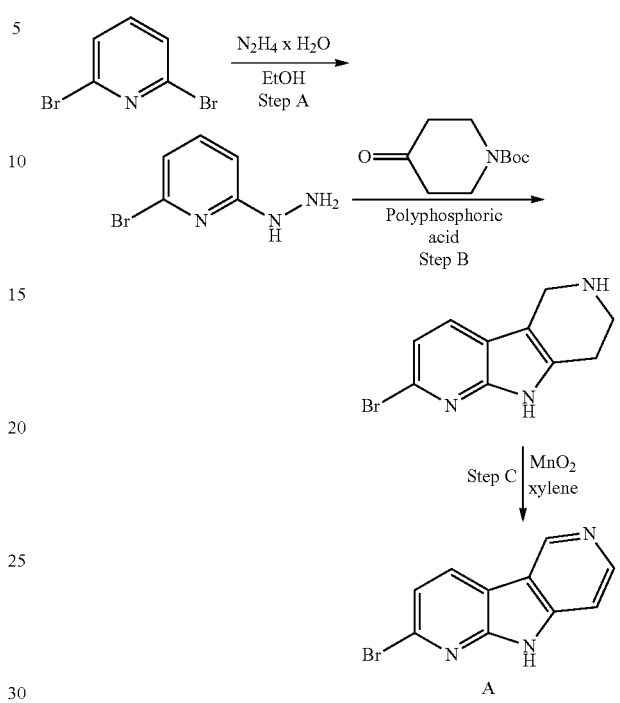

Step A

Commercially available 2,6-dibromopyridine (4.12 g, 16.6 mmol) was suspended in ethanol (40 mL) and hydrazine hydrate (10 mL, 97.6 mmol) in water (~50-60%) was added. The mixture was heated in a sand-bath at ~115° C. for 18 hours. The solvent was removed and the residue was purified by chromatography on silica using ethyl acetate/n-heptane (60/40) to afford the title compound as an off-white solid (3.05 g, 93%).

$^1$H-NMR (400 MHz, CDCl$_3$): δ=7.33 (t, 1H), 6.83 (d, 1H), 6.67 (d, 1H), 6.00 (br-s, 1H), 3.33-3.00 (br-s, 2H)

Step B

The title compound from Step A above (10 g, 53.2 mmol) and commercially available 1-Boc-4-piperidone (10.6 g, 53.2 mmol) were added to a 500 mL flask and mixed to become a homogenous blend. Then polyphosphoric acid (80 g, 115% H$_3$PO$_4$ basis) was added and the mixture was heated at ~160° C. in a sand-bath. At ~120° C. the Boc-protecting group was cleaved resulting in foaming of the reaction mixture. After complete Boc-cleavage the foam collapsed and the dark reaction mixture was stirred at ~160° C. for 20 hours. The reaction was allowed to cool to room temperature and water (400 mL) was added. The reaction mixture was stirred/sonicated until the gummy material was dissolved. The reaction mixture was then placed in an ice-bath and the pH of the solution was adjusted to pH ~12 by adding solid sodium hydroxide pellets (exothermic). The precipitate was collected by filtration and washed with water (400 mL) to remove salts. The precipitate was dissolved in dichloromethane/methanol (9/1; 1500 mL) by sonication and washed with water (2×400 mL) to remove remaining salts and insoluble material. The organic phase was dried over Na$_2$SO$_4$, filtered and the solvents were removed under reduced pressure. The dark residue was treated with dichloromethane (100 mL), sonicated for 5 minutes and the precipitate was collected by filtration. The precipitate was washed with dichloromethane (40 mL) and air-dried to afford the title compound a beige solid (3.5 g, 26%).

¹H-NMR (400 MHz, DMSO-d₆): δ=11.5 (br-s, 1H), 7.72 (d, 1H), 7.15 (d, 1H), 3.86-3.82 (m, 2H), 3.06-3.00 (m, 2H), 2.71-2.65 (m, 2H)

Step C

The title compound from Step B above (1.75 g, 6.94 mmol) was suspended in xylene (380 mL) and manganese (IV) oxide (6.62 g, 76.9 mmol) was added. The reaction mixture was then heated at ~160° C. in a sand-bath for 36 hours. The cooled reaction mixture was evaporated under reduced pressure, the residue suspended in dichloromethane/methanol (1/1; 400 mL) and stirred at room temperature for 30 minutes. The reaction mixture was then filtered through paper filters to remove the manganese (IV) oxide and the filter washed with methanol (50 mL). The combined filtrates were evaporated under reduced pressure and the dark residue purified by chromatography on silica (50 g HP-SIL-cartridge) using a Biotage Isolera system employing an ethyl acetate/heptane gradient (5/95-100/0) to remove unpolar impurities followed by dichloromethane/methanol (9/1→4/1) to afford the title compound as dark yellow solid. The total yield from 2 runs was 1.77 g (51%).

¹H-NMR (400 MHz, DMSO-d₆): δ=12.52 (br-s, 1H), 9.42 (s, 1H), 8.61 (d, 1H), 8.53 (d, 1H), 7.56-7.52 (m, 2H)

Preparative Example B

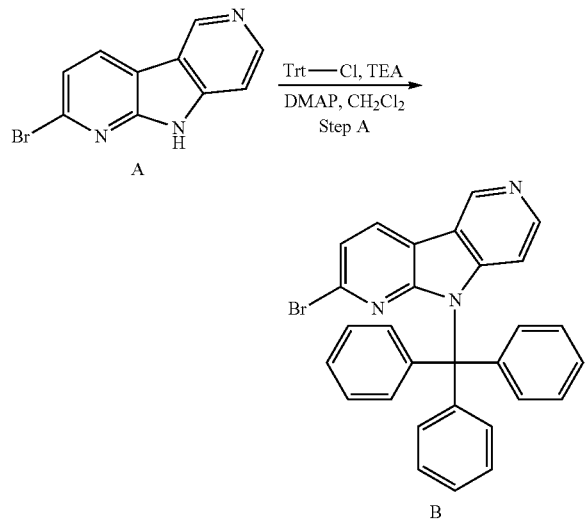

Step A

To a suspension of the title compound from Preparative Example A (0.776 g, 3.13 mmol) in dichloromethane (65 mL) was added triethylamine (1.86 mL, 13 mmol) and trityl-chloride (2.63 g, 9.39 mmol). After the addition of 4-(dimethylamino)-pyridine (0.074 g, 0.608 mmol), the reaction mixture was stirred at room temperature for 16 hours. The reaction mixture was diluted with dichloromethane (150 mL) and water (50 mL). The organic phase was separated, dried over Na₂SO₄, filtered and the solvents removed in vacuo. The residue was purified on HP-Sil SNAP cartridges (50 g) using a Biotage Isolera One purification system employing an ethyl acetate/n-heptane gradient (5/95→100/0→100/0) to afford the title compound B as pale yellow solid (0.831 g, 54%). Unreacted starting material was recovered by flushing the cartridge with ethyl acetate/methanol (90/10) to afford the starting material as off-white solid (0.195 g, 25%).

¹H-NMR (400 MHz, CDCl₃) δ=9.22 (s, 1H), 8.23 (d, 1H), 8.13 (d, 1H), 7.48-7.42 (m, 7H), 7.33-7.22 (m, 12H), 6.41 (d, 1H)

MS (ESI); m/z=490.03/491.96 [M+H]⁺

Example 1

Step A

To a mixture of degassed 1,4-dioxane (4.3 mL) and water (1 mL) in a microwave vial was added [1,1'-bis(diphenylphosphino)ferrocene]dichloropalladium(II), complex with dichloromethane (0.0084 g, 0.01 mmol), followed by the title compound from Preparative Example A (0.05 g, 0.2 mmol), (2-fluoropyridin-3-yl)boronic acid (0.035 g, 0.245 mmol) and cesium carbonate (0.133 g, 0.41 mmol). The reaction mixture was then heated at ~110° C. in a sand-bath for 16 hours. The reaction mixture was diluted with ethyl acetate (60 mL) and water (20 mL), the organic phase was separated, dried over Na₂SO₄, filtered and the solvents were evaporated in vacuo. The dark residue was purified by chromatography on silica (10 g HP-SIL) using a Biotage Isolera system employing a dichloromethane/methanol gradient (100/0→95/5→90/10) to afford a mixture of the title compound and unreacted starting material. The mixture was further purified by two times preparative TLC (500 μM Analtech Uniplate (20×20 cm)) using dichloromethane/methanol (9/1) as mobile phase to afford the title compound F-4 as a white solid (0.0039 g, 7.3%).

¹H NMR (400 MHz, DMSO-d₆) δ=12.45 (br-s, 1H), 8.78 (d, 1H), 8.62-8.52 (m, 2H), 8.37-8.35 (m, 1H), 7.84 (dd, 1H), 7.61-7.57 (m, 1H), 7.57 (d, 1H)

MS (ESI): m/z=265.01 [M+H]⁺

Example 2

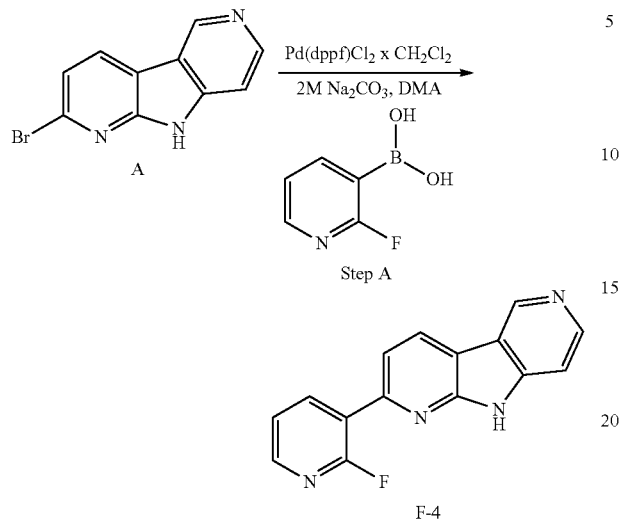

Step A

In a 5 ml microwave tube was dissolved the title compound from Preparative Example A (0.05 g, 0.202 mmol) and (2-fluoropyridin-3-yl)boronic acid (0.0568 g, 0.403 mmol) in N,N'-dimethylacetamide (Volume: 2.015 mL). Sodium carbonate 2 M (0.403 mL, 0.806 mmol) was added and the resulting stirring solution was degassed for 5 minutes. [1,1'-Bis(diphenylphosphino)ferrocene]dichloropalladium(II) complex with dichloromethane was added (0.017 g, 0.02 mmol) and the reaction mixture was heated to 110° C. for 3 hours. TLC monitoring showed completion of the reaction. The reaction mixture was diluted with ethyl acetate, after insolubles were filtered out, the filtrate was washed with water and brine. The organic layer was dried with MgSO$_4$, filtered and concentrated. The residue was purified by chromatography on silica (10 g HP-SIL) using a Biotage Isolera system employing a dichloromethane/methanol gradient (100/0→90/10) to afford the title compound F-4 as a beige solid (0.028 g, 54%).

$^1$H-NMR (400 MHz, DMSO-d$_6$) δ=12.45 (s, 1H), 9.43 (s, 1H), 8.77 (d, 1H), 8.66-8.45 (m, 2H), 8.35 (d, 1H), 7.83 (dd, 1H), 7.64-7.39 (m, 2H)

MS (ESI); m/z=265.19 [M+H]$^+$

Example 3

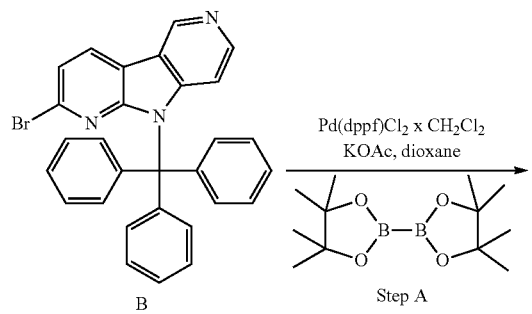

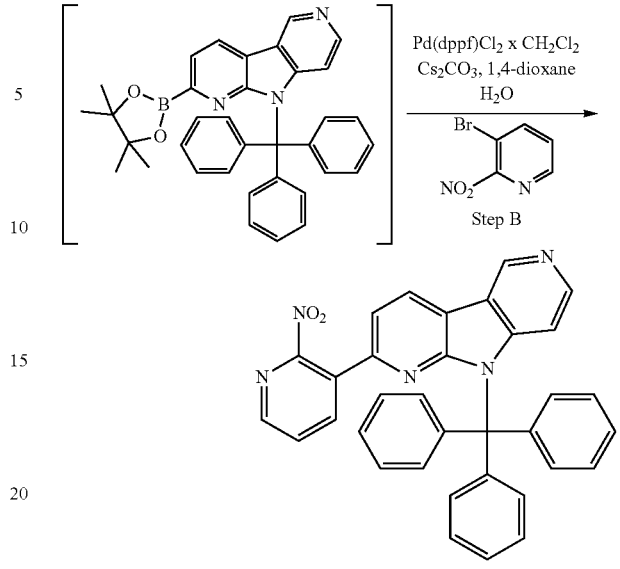

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over Na$_2$SO$_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)dichloro-palladium(II), complex with dichloromethane (0.034 g, 0.04 mmol), 3-bromo-2-nitropyridine (0.1 g, 0.49 mmol) and cesium carbonate (0.266 g, 0.82 mmol) were added and the reaction mixture was heated at ~115° C. in a sand-bath for 6 hours.

The reaction mixtures of 4 runs as described in Steps A and B were combined and diluted with ethyl acetate (600 mL) and water (200 mL), the organic phase separated, dried over Na$_2$SO$_4$, filtered and the solvents evaporated in vacuo. The dark residue was split in two portions and each portion was purified by chromatography on silica (40 g BGB-column, Interchim) using a Biotage Isolera system employing an ethyl acetate/n-heptane gradient (5/95→100/0→100/0) to afford a mixture of the more polar title compound and a less polar byproduct. The mixture (0.260 g) was further purified by preparative TLC with a loading of ~0.03 g of mixture per 1000 μM Analtech Uniplate (20×20 cm) using ethyl acetate/n-heptane (70/30) as mobile phase to afford the more polar title compound 14 as pale yellow solid (0.1 g, 11.8%).

More polar title compound 14:

$^1$H NMR (400 MHz, CDCl$_3$) δ=9.28 (s, 1H), 8.48-8.46 (m, 1H); 8.38 (d, 1H), 8.26 (d, 1H), 7.55-7.53 (m, 1H). 7.52-7.46 (m, 6H), 7.32-7.20 (m, 11H), 6.46 (d, 1H)

MS (ESI): m/z=534.17 [M+H]$^+$.

Example 4

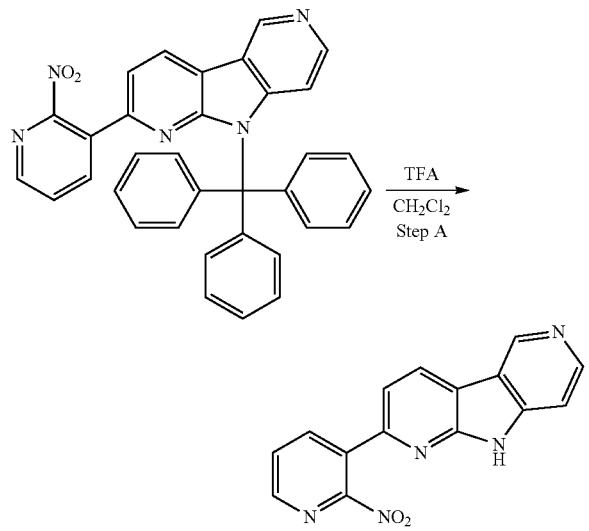

Step A

The title compound from Example 3 (compound 14; 0.0434 g, 0.082 mmol) was dissolved in dichloromethane (5 mL) and trifluoroacetic acid (1.2 mL) was added. The reaction mixture was stirred at room temperature for 6 hours. The reaction mixture was diluted with diluted with dichloromethane (50 mL) and water (20 mL). The pH of the aqueous phase was adjusted to pH-12 by the addition of a 1 M aqueous sodium hydroxide solution. The aqueous layer was separated, extracted with dichloromethane (25 mL), the combined organic layer dried over Na$_2$SO$_4$, filtered and the solvent removed under reduced pressure. The residue was purified by chromatography on silica (10 g HP-SIL-column) using a Biotage Isolera system employing a dichloromethane/methanol gradient (100/0→95/5→90/10→80/20) to afford the title compound as an off-white solid (0.0199 g, 83%)

$^1$H NMR (400 MHz, DMSO-d$_6$) δ=12.45 (br-s, 1H), 9.45 (s, 1H), 8.85 (s, 1H), 8.67 (dd, 1H), 8.58 (dd, 1H), 8.54 (d, 1H), 7.97 (dd, 1H); 7.82 (d, 1H), 7.50 (d, 1H)

MS (ESI): m/z=291.81 [M+H]$^+$.

Example 5

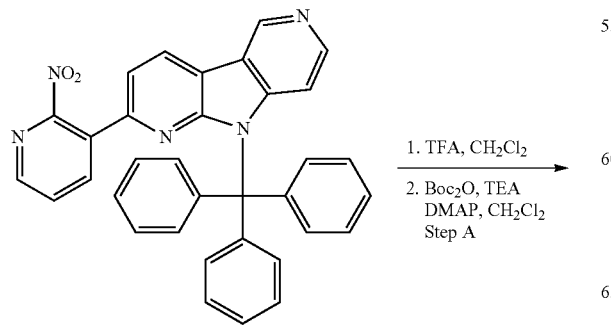

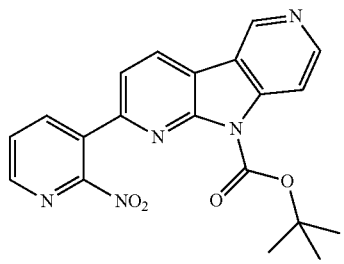

Step A

To a solution of the title compound from Example 3 (compound 14; 0.038 g, 0.071 mmol) in dichloromethane (5 mL) was added trifluoroacetic acid (1.2 mL). The reaction mixture was stirred at room temperature for 6 hours and methanol (2 mL) was added. The solvents were evaporated in vacuo and the residue dissolved/suspended in methanol (5 mL). The solvents were evaporated in vacuo and the residue dissolve/suspended in methanol (5 mL). The solvents were evaporated in vacuo and the residue suspended in dichloromethane (2 mL). After the addition of triethylamine (1 mL, 7.2 mmol), di-tert-butyl dicarbonate (0.098 g, 0.43 mmol), and 4-(dimethylamino)-pyridine (0.0018 g, 0.014 mmol), the reaction mixture was stirred at room temperature for 18 hours. The reaction mixture was diluted with ethyl acetate (50 mL) and water (20 mL). The organic phase was separated, dried aver Na$_2$SO$_4$, filtered and the solvents removed in vacuo. The residue was purified on silica (25 g puriFlash, Interchim) using a Biotage Isolera One purification system employing an ethyl acetate/n-heptane gradient (5/95→100/0→100/0) to afford the title compound as pale yellow solid (0.0184 g, 66%).

$^1$H-NMR (400 MHz, CDCl$_3$) δ=9.34 (s, 1H), 8.75 (d, 1H), 8.65-8.62 (m, 1H), 8.50 (d, 1H), 8.33 (d, 1H); 8.26 (d, 1H), 7.76-7.72 (m, 1H), 7.62 (d, 1H), 1.77 (s, 9H) MS (ESI); m/z=392.33 [M+H]$^+$

Comparative Example 2 (F-2)

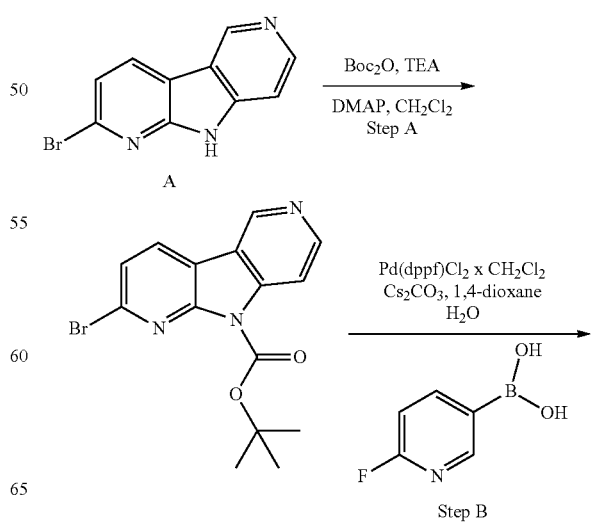

-continued

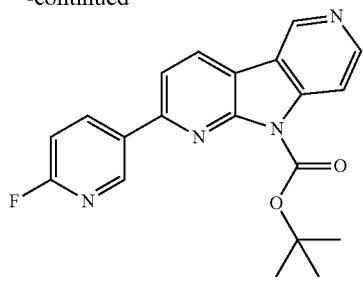

less polar

+

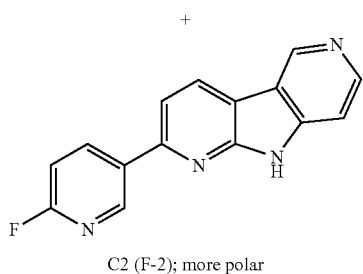

C2 (F-2); more polar

Step A

To a suspension of the title compound from Preparative Example A (0.430 g, 1.73 mmol) in dichloromethane (25 mL) was added triethylamine (1.93 mL, 13.89 mmol) and di-tert-butyl dicarbonate (2.27 g, 10.02 mmol). After the addition of 4-(dimethylamino)-pyridine (0.042 g, 0.34 mmol), the reaction mixture was stirred at room temperature for 3 days. The solvents were removed under reduced pressure and the residue was purified on HP-Sil SNAP cartridges (25 g) using a Biotage Isolera One purification system employing an ethyl acetate/n-heptane gradient (5/95→100/0→100/0) to afford the title compound as off-white solid (0.558 g, 92%).

$^1$H-NMR (400 MHz, CDCl$_3$) δ=9.28 (s, 1H), 8.73 (d, 1H), 8.22 (d, 2H), 7.59 8d, 1H), 1.80 (s, 9H)

Step B

To a mixture of degassed 1,4-dioxane (3 mL) and water (0.7 mL) in a microwave vial was added [1,1'-bis(diphenylphosphino)ferrocene]dichloropalladium(II), complex with dichloromethane (0.0058 g, 0.007 mmol), followed by the title compound from Step A above (0.05 g, 0.143 mmol), (6-fluoropyridin-3-yl)boronic acid (0.024 g, 0.17 mmol) and cesium carbonate (0.092 g, 0.286 mmol). The reaction mixture was then heated at ~100° C. in a sand-bath for 4 hours. The reaction mixture was diluted with ethyl acetate (80 mL) and water (35 mL), the organic phase separated, dried over Na$_2$SO$_4$, filtered and the solvents evaporated in vacuo. The dark residue was purified by chromatography on silica (12 g, puriFlash, Interchim) using a Biotage Isolera system employing a dichloromethane/methanol gradient (100/0→98/2→95/5→90/10→80/20) to afford the less polar Boc-protected compound (0.0255 g, 49%) and the more polar Comparative Example C2 (F-2) as off-white solid (0.0116 g, 31%).

More Polar Comparative Example C2 (F-2):

$^1$H NMR (400 MHz, DMSO-d$_6$) δ=12.40 (br-s, 1H), 9.40 (s, 1H), 9.05 (s, 1H), 8.78-8.70 (m, 2H), 8.51 (d, 1H), 8.02 (d, 1H), 7.50 (d, 1H), 7.36 (dd, 1H)

MS (ESI): m/z=265.09 [M+H]$^+$

Less Polar Boc-Protected Compound:

$^1$H NMR (400 MHz, DMSO-d$_6$) δ=9.48 (s, 1H), 9.13 (d, 1H), 8.84-8.78 (m, 2H), 8.68 (d, 1H), 8.23 (d, 1H), 8.19 (d, 1H), 7.40 (dd, 1H), 1.75 8s, 9H)

The synthesis of Comparative Example C2 (F-2) was first described in WO2015/052105 (Example 1) by a different synthesis.

Comparative Example 2 (F-2) Precursor

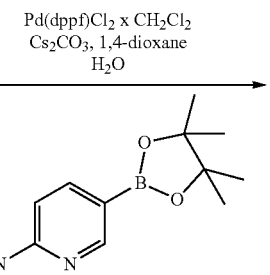

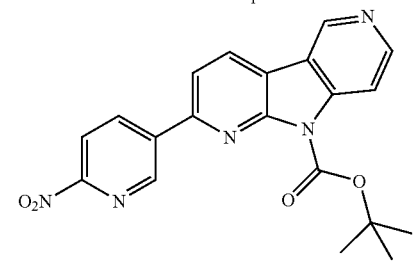

C2 (F-2) Precursor

Step A

To a mixture of degassed 1,4-dioxane (3 mL) and water (0.7 mL) in a microwave vial was added [1,1'-bis(diphenylphosphino)ferrocene]dichloropalladium(II), complex with dichloromethane (0.0058 g, 0.007 mmol), followed by the title compound from Comparative Example 2 Step A (0.05 g, 0.143 mmol), 2-nitro-5-(4,4,5,5-tetramethyl-1,3,2-dioxaborolan-2-yl)pyridine (0.0428 g, 0.17 mmol) and cesium carbonate (0.092 g, 0.286 mmol). The reaction mixture was then heated at ~100° C. in a sand-bath for 4 hours. The reaction mixture was diluted with ethyl acetate (80 mL) and water (35 mL), the organic phase separated, dried over Na$_2$SO$_4$, filtered and the solvents evaporated in vacuo. The dark residue was purified by chromatography on silica (12 g, puriFlash, Interchim) using a Biotage Isolera system employing a dichloromethane/methanol gradient (100/0→98/2→95/5→90/10→80/20) to afford the Comparative Example C2 (F-2) Precursor as a pale yellow solid (0.0173 g, 31%).

$^1$H NMR (400 MHz, CDCl$_3$/CD$_3$OD) δ=9.45 (d, 1H), 9.32 (s, 1H), 8.93 (dd, 1H), 8.68-8.64 (m, 2H), 8.46 (d, 1H), 8.35 (d, 1H), 8.14 (d, 1H), 1.82 (s, 9H)

MS (ESI): m/z=392.13 [M+H]$^+$

The synthesis of Comparative Example C2 (F-2) precursor was first described in WO2015/052105 (Example 3a) by a different synthesis.

Comparative Example 5 (F-5)

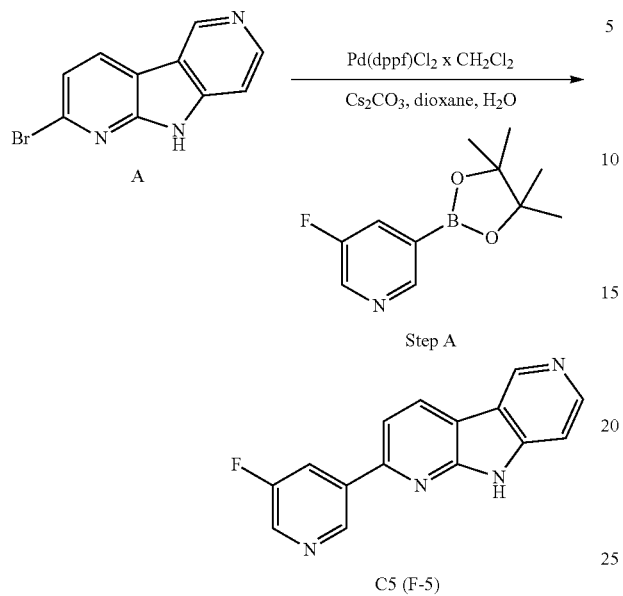

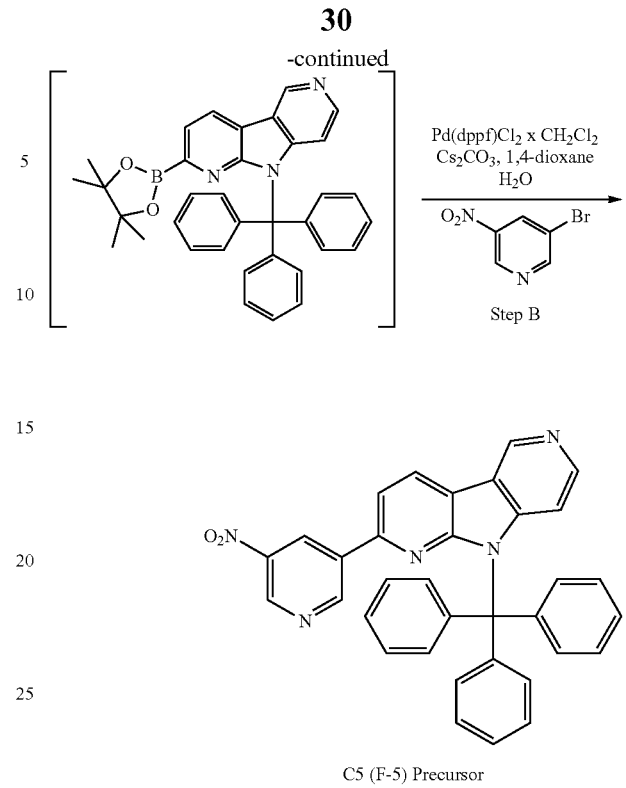

Step A

To a mixture of degassed 1,4-dioxane (4.3 mL) and water (1 mL) in a microwave vial was added [1,1'-bis(diphenylphosphino)ferrocene]dichloropalladium(II), complex with dichloromethane (0.0084 g, 0.01 mmol), followed by the title compound from Preparative Example A (0.05 g, 0.2 mmol), 3-fluoro-5-(4,4,5,5-tetramethyl-1,3,2-dioxaborolan-2-yl)pyridine (0.055 g, 0.246 mmol) and cesium carbonate (0.133 g, 0.41 mmol). The reaction mixture was then heated at ~115° C. in a sand-bath for 6 hours. The reaction mixture was diluted with ethyl acetate (60 mL) and water (20 mL), the organic phase separated, dried over $Na_2SO_4$, filtered and the solvents evaporated in vacuo. The dark residue was purified by chromatography on silica (25 g HP-SIL) using a Biotage Isolera system employing a dichloromethane/methanol gradient (100/0→95/5→90/10→80/20) to afford the Comparative Example C5 (F-5) as off-white solid (0.022 g, 43%).

$^1$H NMR (400 MHz, DMSO-$d_6$) δ=12.45 (br-s, 1H), 9.45 (s, 1H), 9.31 (s, 1H), 8.80 (d, 1H), 8.67 (d, 1H). 8.53 (d, 1H), 8.46-8.40 (m, 1H), 8.11 (d, 1H), 7.52 (d, 1H) MS (ESI): m/z=265.06 [M+H]$^+$

Comparative Example 5 (F-5) Precursor

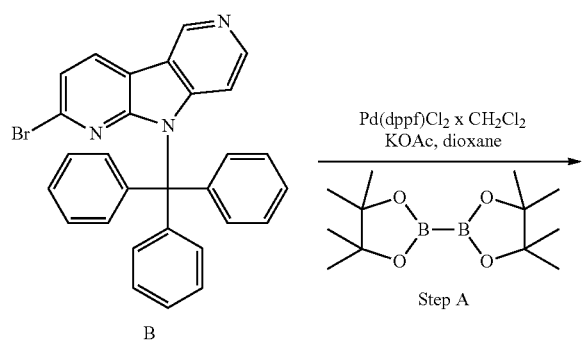

Step A

To a mixture of degassed 1,4-dioxane (4 mL) in a microwave vial was added [1,1'-bis(diphenylphosphino)ferrocene]dichloropalladium(II), complex with dichloromethane (0.017 g, 0.02 mmol), followed by the title compound from Preparative Example B (0.1 g, 0.2 mmol), bis(pinacolato)diborane (0.056 g, 0.22 mmol) and potassium acetate (0.059 g, 0.6 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (4.3 mL) and water (1 mL) in a microwave vial. Then [1,1'-bis(diphenylphosphino)ferrocene]dichloro-palladium(II), complex with dichloromethane (0.017 g, 0.02 mmol), 3-bromo-5-nitropyridine (0.05 g, 0.245 mmol) and cesium carbonate (0.133 g, 0.41 mmol) were added and the reaction mixture was heated at ~115° C. in a sand-bath for 6 hours.

The reaction mixture was diluted with ethyl acetate (80 mL) and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0→100/0) to afford the Comparative Example C5 (F-5) Precursor as pale yellow solid (0.0144 g, 13%).

$^1$H NMR (400 MHz, CDCl$_3$) δ=9.36 (d, 1H), 9.30 (s, 1H), 9.02 (d, 1H); 8.52-8.48 (m, 2H); 8.29 (d, 1H), 7.80 (d, 1H), 7.60-7.55 (m, 5H), 7.33-7.25 (m, 10H), 6.46 (d, 1H) MS (ESI): m/z=533.67 [M+H]$^+$.

Comparative Example 6 (F-6)

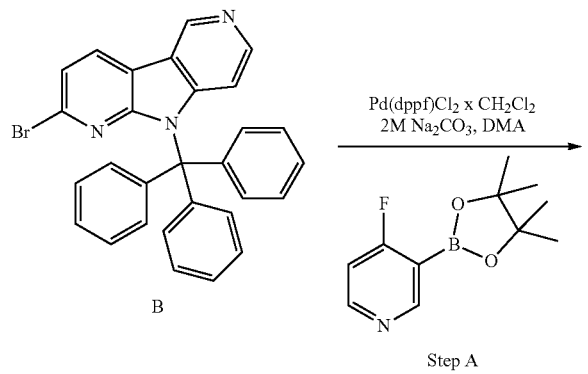

Step A

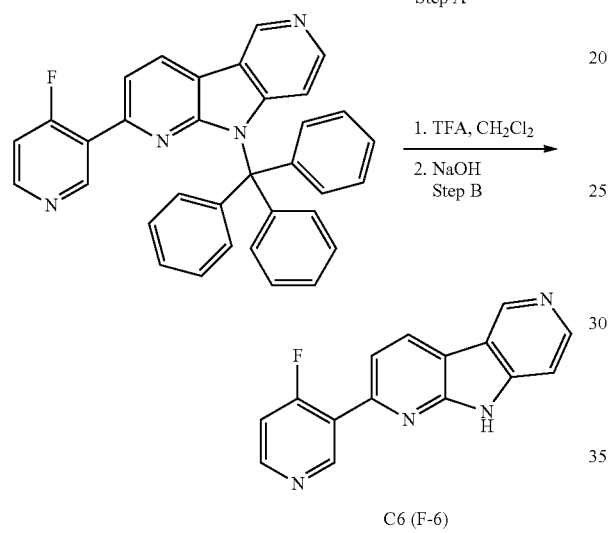

C6 (F-6)

Step A

In a 20 ml microwave tube was dissolved the title compound from Preparative Example B (0.2 g, 0.408 mmol) and 4-fluoro-3-(4,4,5,5-tetramethyl-1,3,2-dioxaborolan-2-yl) pyridine (0.182 g, 0.816 mmol) in N,N'-dimethylacetamide (5.10 mL). Sodium carbonate (0.816 ml, 1.631 mmol) was added and the resulting stirring solution was degassed for 5 minutes. Then [1,1'-bis(diphenylphosphino)ferrocene]dichloropalladium(II) complex with dichloromethane was added and the reaction mixture was heated to 110° C. for 22 hours. TLC monitoring showed completion of the reaction. The reaction mixture was diluted with dichloromethane, insolubles were filtered out through Celite, and the filtrate was washed with water three times to remove residual amounts of N,N'-dimethylacetamide. The organic layer was dried MgSO$_4$, filtered and concentrated. The residue was purified via Biotage Isolera One (100:0 to 90:10 dichloromethane/methanol; 25 g HP-Sil column) to give afford the title compound (0.1036 g; 50%).

$^1$H-NMR (400 MHz, DMSO-d$_6$) δ=9.43 (s, 1H), 8.75 (d, 1H), 8.54 (dd, 1H), 8.26 (d, 1H), 8.17 (d, 1H), 7.83 (dd, 1H), 7.61-7.52 (m, 6H), 7.41 (dd, 1H), 7.35-7.20 (m, 9H), 6.46 (d, 1H).

MS [M+H]$^+$=507.43, 243.29

Step B

In a 25 ml round bottom flask, was dissolved the title compound from Step A above (0.1 g, 0.199 mmol) in dichloromethane (1 mL). Trifluoroacetic acid (1 mL) was carefully added and the reaction mixture was stirred for 18 hours at room temperature. After cooling at 0° C., the reaction mixture was quenched to pH=10 with 2 M sodium hydroxide solution. The resulting suspension was filtered. The reaction mixture was washed with water and brine. The organic was dried over MgSO$_4$, filtered and concentrated. The residue was purified via Biotage Isolera One (100:0 to 90:10 dichloromethane/methanol; 10 g HP-Sil column) to give afford the Comparative Example C6 (F-6) (0.026 g; 47%).

$^1$H-NMR (400 MHz, DMSO-d$_6$) δ 12.57 (s, 1H), 9.46 (s, 1H), 9.19 (d, 1H), 8.80 (d, 1H), 8.70 (s, 1H), 8.59-8.52 (m, 1H), 7.81 (d, 1H), 7.55 (d, 2H)

MS [M+H]$^+$=265.29

Comparative Example 6 (F-6) Precursor

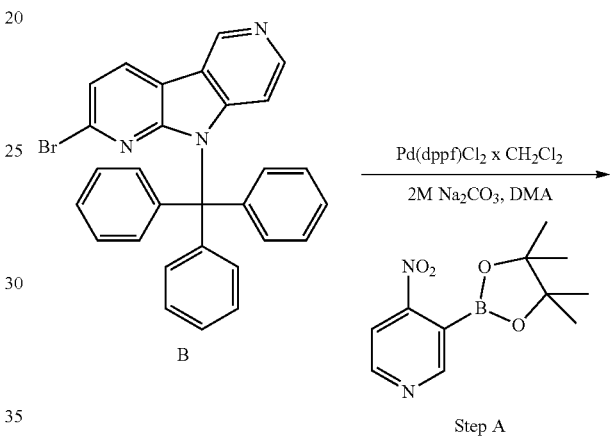

Step A

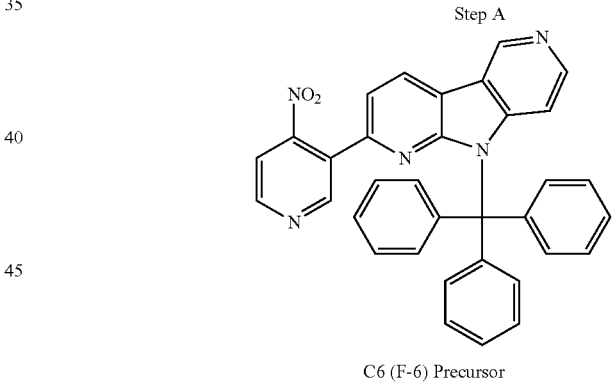

C6 (F-6) Precursor

In a 20 ml microwave tube was dissolved the title compound from Preparative Example B (0.2 g, 0.408 mmol) and 4-nitro-3-(4,4,5,5-tetramethyl-1,3,2-dioxaborolan-2-yl) pyridine (0.204 g, 0.816 mmol) in N,N'-dimethylacetamide (5.10 mL). Sodium carbonate (0.816 ml, 1.631 mmol) was added and the resulting stirring solution was degassed for 5 minutes. Then [1,1'-bis(diphenylphosphino)ferrocene]dichloropalladium(II) complex with dichloromethane was added (0.017 g, 0.02 mmol) and the reaction mixture was heated to 110° C. for 22 hours. TLC monitoring showed completion of the reaction. The reaction mixture was diluted with dichloromethane, insolubles were filtered out through Celite, and the filtrate was washed with water three times to remove residual amounts of N,N'-dimethylacetamide. The organic layer was dried MgSO$_4$, filtered and concentrated. The residue was purified via Biotage Isolera One employing an ethyl acetate/n-heptane gradient (5/95→100/0→100/0) to afford the Comparative Example C6 (F-6) Precursor as pale yellow solid (0.056 g, 28%).

¹H-NMR (400 MHz, DMSO-d₆) δ=9.45 (s, 1H), 8.81 (d, 1H), 8.69 (d, 1H), 8.32-8.23 (m, 3H), 8.20 (d, 1H), 7.60 (dd, 6H), 7.36-7.22 (m, 9H), 6.52 (d, 1H), 5.76 (s, 1H).

MS (ESI): m/z=533.87 [M+H]⁺.

Comparative Example 7 (F-7)

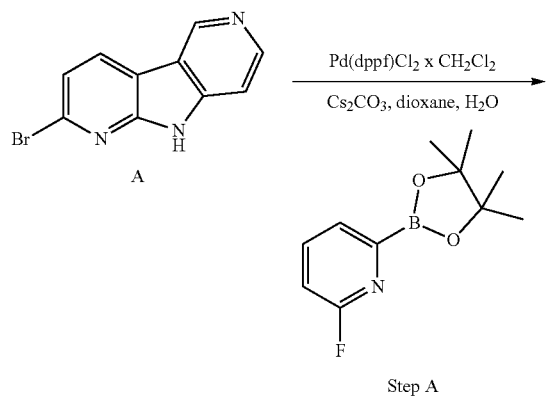

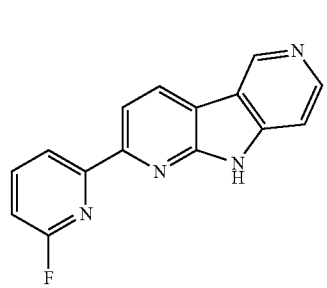

C7 (F-7)

Comparative Example 7 (F-7) Precursor

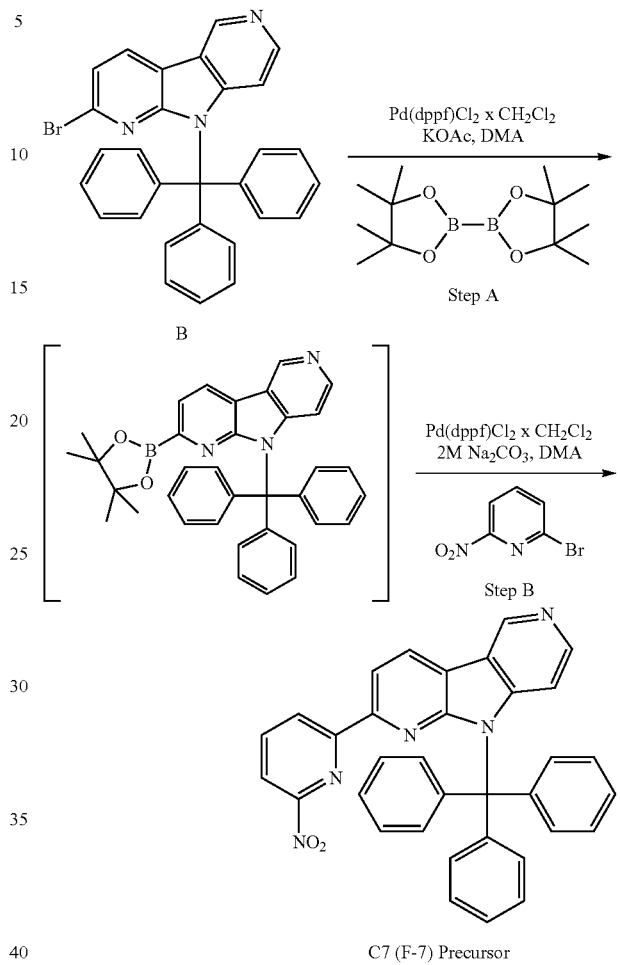

C7 (F-7) Precursor

Step A

To a mixture of degassed 1,4-dioxane (4.3 mL) and water (1 mL) in a microwave vial was added [1,1-bis(diphenylphosphino)ferrocene]dichloropalladium(II), complex with dichloromethane (0.0084 g, 0.01 mmol), followed by the title compound from Preparative Example A (0.05 g, 0.2 mmol), 2-fluoro-6-(4,4,5,5-tetramethyl-1,3,2-dioxaborolan-2-yl)pyridine (0.055 g, 0.246 mmol) and cesium carbonate (0.133 g, 0.41 mmol). The reaction mixture was then heated at ~115° C. in a sand-bath for 6 hours. The reaction mixture was diluted with ethyl acetate (60 mL) and water (20 mL), the organic phase separated, dried over Na₂SO₄, filtered and the solvents evaporated in vacuo. The dark residue was purified by chromatography on silica (25 g HP-SIL) using a Biotage Isolera system employing a dichloromethane/methanol gradient (100/0→95/5→90/10→80/20) to afford the Comparative Example C7 (F-7) as off-white solid (0.033 g, 63%).

¹H NMR (400 MHz, DMSO-d₆) δ=12.42 (s, 1H), 9.41 (s, 1H), 8.77 (d, 1H), 8.52 (d, 1H), 8.40 (dd, 1H), 8.27 (d, 1H), 8.18 (q, 1H), 7.51 (d, 1H), 7.26 (dd, 1H)

MS (ESI): m/z=265.09 [M+H]⁺

Step A

To a mixture of degassed N,N'-dimethylacetamide (4 mL) in a microwave vial was added [1,1'-bis(diphenylphosphino)ferrocene]dichloropalladium(II), complex with dichloromethane (0.017 g, 0.02 mmol), followed by the title compound from Preparative Example B (0.1 g, 0.2 mmol), bis(pinacolato)diborane (0.056 g, 0.22 mmol) and potassium acetate (0.059 g, 0.6 mmol). The reaction mixture was then heated at ~95° C. in a sand-bath for 18 hours. The reaction mixture was diluted with ethyl acetate (100 mL) and water (30 mL), the organic phase separated, dried over Na₂SO₄, filtered and the solvents evaporated in vacuo to afford the crude title compound which was directly used in the next step.

Step B

In a 20 ml microwave tube was dissolved the crude title compound from Step A above, 2-bromo-6-nitropyridine (0.05 g, 0.245 mmol) in N,N'-dimethylacetamide (5.10 mL). Sodium carbonate (0.408 ml, 0.816 mmol) was added and the resulting stirring solution was degassed for 5 minutes. Then [1,1'-bis(diphenylphosphino)ferrocene]dichloropalladium(II) complex with dichloromethane was added (0.017 g, 0.02 mmol) and the reaction mixture was heated to 110° C. for 22 hours. TLC monitoring showed completion of the reaction. The reaction mixture was diluted with dichloromethane, insolubles were filtered out through Celite, and the filtrate was washed with water three times to remove residual amounts of N,N'-dimethylacetamide. The organic layer was dried MgSO$_4$, filtered and concentrated. The residue was purified via Biotage Isolera One employing an ethyl acetate/n-heptane gradient (5/95→100/0→100/0) to afford the Comparative Example C7 (F-7) Precursor as pale yellow solid (0.0174 g, 16%).

$^1$H-NMR (400 MHz, DMSO-d$_6$) δ=9.43 (s, 1H), 9.38 (s, 1H), 8.81 (d, 1H), 8.60 (dd, 1H), 8.33 (d, 1H), 8.28-8.24 (m, 2H), 8.18 (d, 1H), 8.10 (t, 1H), 7.61 (d, 7H), 7.47 (d, 4H), 7.42 (d, 1H), 7.28 (tt, 18H), 6.58 (d, 1H), 6.19 (d, 1H) MS (ESI): m/z=533.62 [M+H]$^+$.

Comparative Example 8 (F-8)

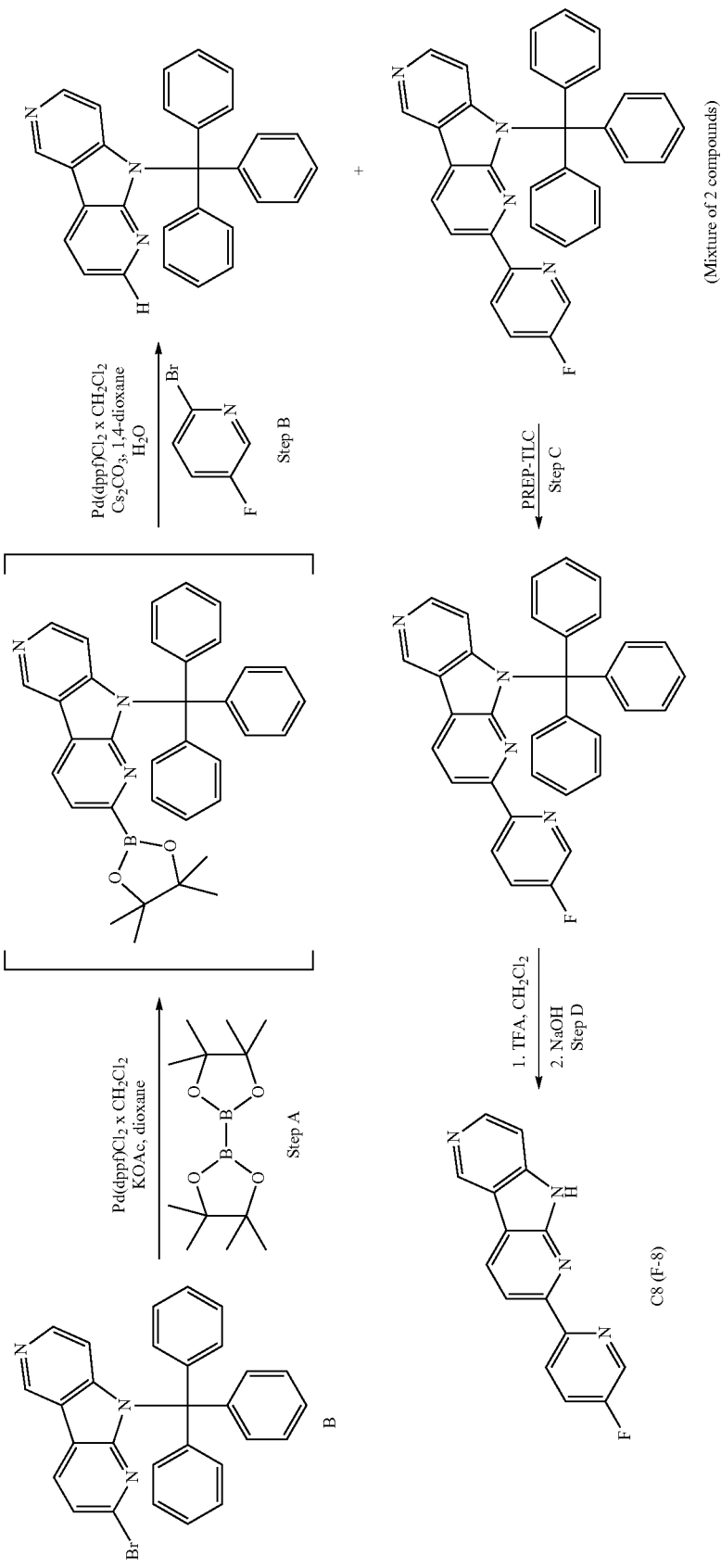

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)ferrocene]dichloro-palladium(II), complex with dichloromethane (0.034 g, 0.04 mmol), 2-bromo-5-fluoropyridine (0.086 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL) and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0→100/0) to afford a mixture of the title compound and byproduct (0.064 g).

Step C

The mixture of the title compound and byproduct from Step B above (0.064 g) was purified by preparative TLC with a loading of ~0.03 g of mixture per 1000 μM Analtech Uniplate (20×20 cm) using dichloromethane/acetone (90/10) as mobile phase to afford the more polar title compound as off-white solid (0.0385 g, 18.5% for 3 steps).

$^1$H NMR (400 MHz, CDCl$_3$) δ=9.26 (s, 1H), 8.45 (d, 1H), 8.38 (AB-system, 2H), 8.25 (d, 1H), 7.62-7.58 (m, 5H), 7.30-7.18 (m, 12H), 6.56 (d, 1H)

Step D

The title compound from Step C above (0.0385 g, 0.076 mmol) was dissolved in dichloromethane (5 mL) and trifluoroacetic acid (1.2 mL) was added. The reaction mixture was stirred at room temperature for 6 hours. The reaction mixture was diluted with diluted with dichloromethane (50 mL) and water (20 mL). The pH of the aqueous phase was adjusted to pH-12 by the addition of a 1 M aqueous sodium hydroxide solution. The aqueous layer was separated, extracted with dichloromethane (25 mL), the combined organic layer dried over $Na_2SO_4$, filtered and the solvent removed under reduced pressure. The residue was purified by chromatography on silica (10 g HP-SIL-column) using a Biotage Isolera system employing a dichloromethane/methanol gradient (100/0→95/5→90/10) to afford the Comparative Example C8 (F-8) as a white solid (0.0079 g, 39.3%)

$^1$H NMR (400 MHz, DMSO-d$_6$) δ=12.40 (br-s, 1H), 9.40 (s, 1H), 8.77 (d, 1H), 8.72 (d, 1H), 8.55-8.50 (m, 2H), 8.35 (d, 1H), 7.95-7.90 (m, 1H), 7.51 (d, 1H)

MS (ESI): m/z=265.06 [M+H]$^+$.

The synthesis of Comparative Example C8 (F-8) was first described in WO2016/124508 (Example 18) by a different synthesis.

Comparative Example 8 (F-8) Precursor

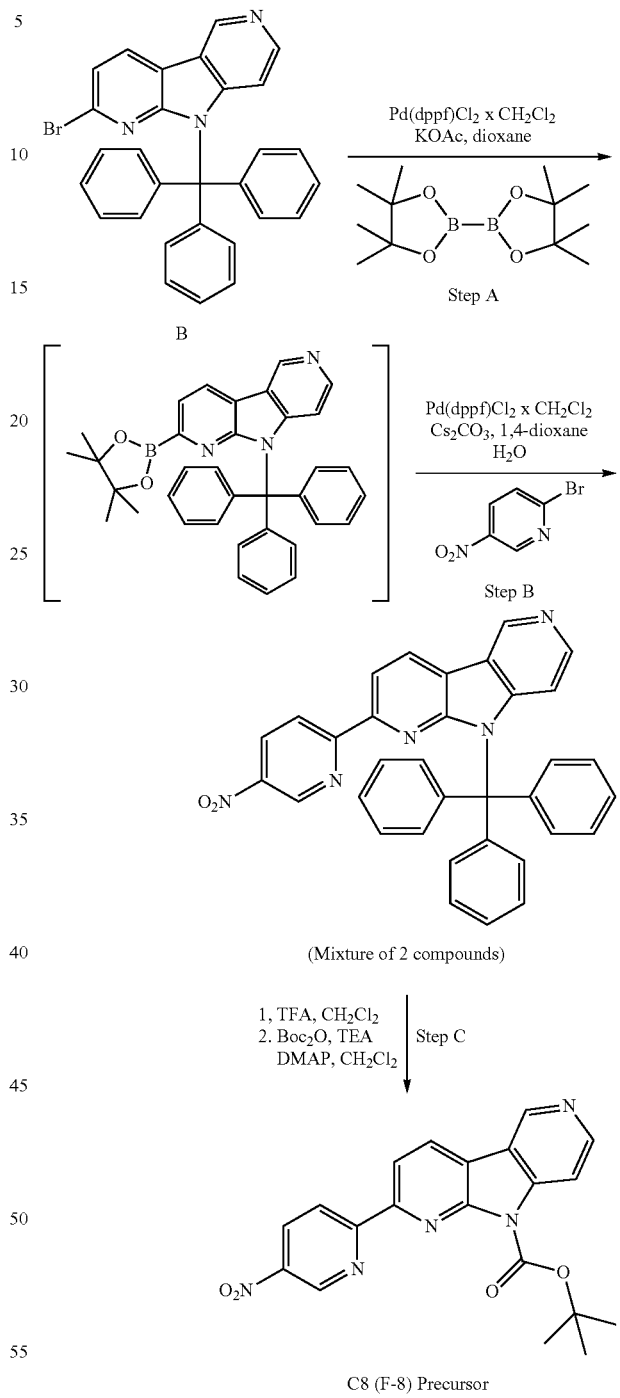

C8 (F-8) Precursor

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over Na$_2$SO$_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)ferrocene]dichloro-palladium(II), complex with dichloromethane (0.034 g, 0.04 mmol), 2-bromo-5-nitropyridine (0.1 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL) and water (30 mL), the organic phase separated, dried over Na$_2$SO$_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0 →100/0) to afford a mixture of the title compound and byproduct (0.0788 g).

Step C

The mixture of the title compound from Step B above and byproduct (0.0788 g) was dissolved in dichloromethane (10 mL) and trifluoroacetic acid (2.4 mL) was added. The reaction mixture was stirred at room temperature for 6 hours and then methanol was added (10 mL). The solvents were evaporated in vacuo and the residue suspended in methanol (10 mL). The solvents were again evaporated in vacuo and the residue suspended in dichloromethane (4 mL). After the addition of triethylamine (2 mL, 14.4 mmol), di-tert-butyl dicarbonate (0.2 g, 0.86 mmol), and 4-(dimethylamino)-pyridine (0.0036 g, 0.028 mmol), the reaction mixture was stirred at room temperature for 18 hours. The reaction mixture was diluted with ethyl acetate (100 mL) and water (40 mL). The organic phase was separated, dried over Na$_2$SO$_4$, filtered and the solvents removed in vacuo. The residue was purified on silica (25 g puriFlash, Interchim) using a Biotage Isolera One purification system employing an ethyl acetate/n-heptane gradient (5/95→100/0→100/0) to afford the Comparative Example C8 (F-8) Precursor as pale yellow solid (0.0149 g, 25.7%).

$^1$H NMR (400 MHz, CDCl$_3$) δ=9.55 (d, 1H), 9.36 (s, 1H), 8.88 (d, 1H), 8.77 (d, 1H), 8.72 (d, 1H), 8.65 (dd, 1H), 8.56 (d, 1H), 8.30 (d, 1H), 1.87 (s, 9H)

MS (ESI): m/z=391.93 [M+H]$^+$.

Comparative Example 9 (F-9)

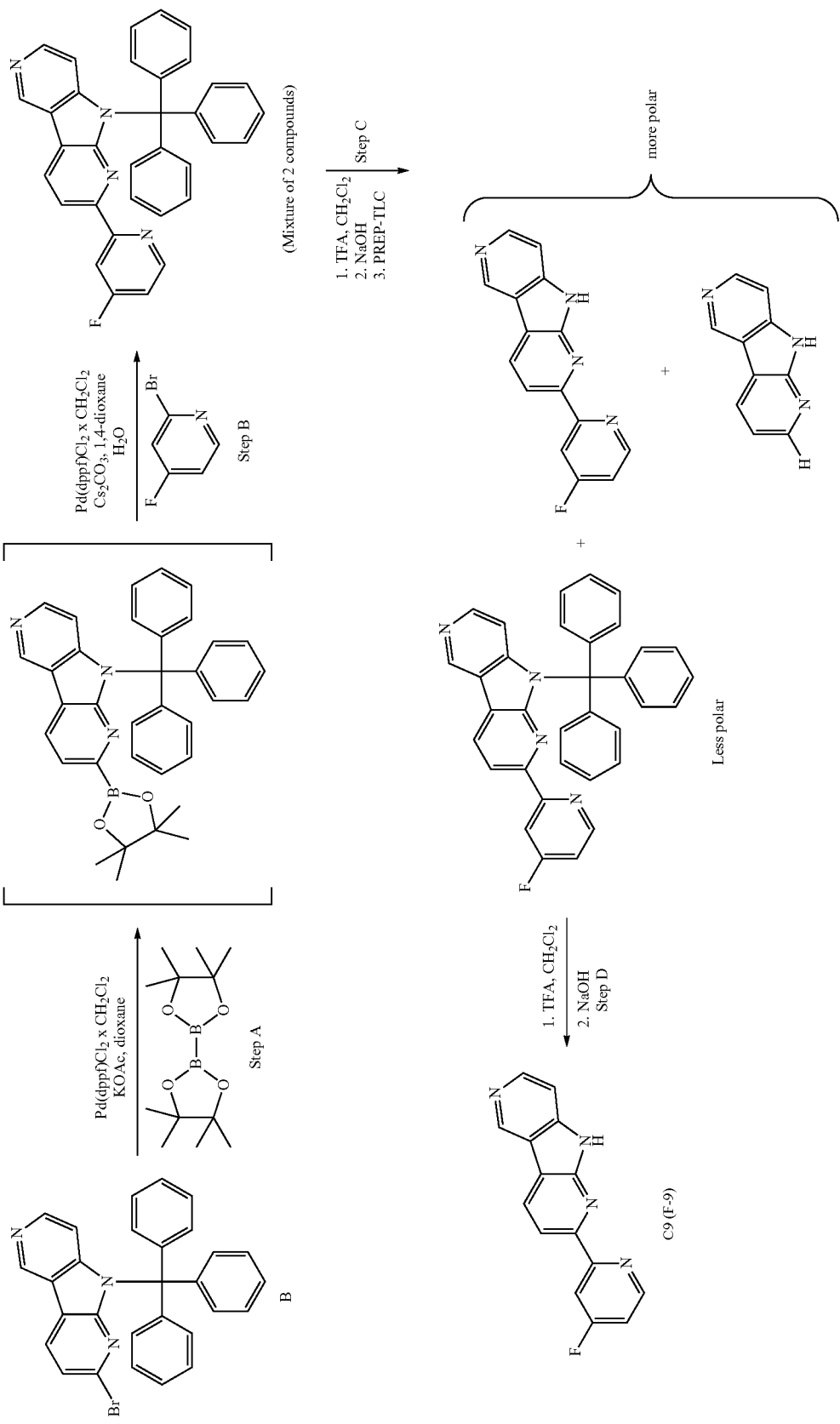

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato) diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1-bis(diphenylphosphino)ferrocene]dichloro-palladium(II), complex with dichloromethane (0.034 g, 0.04 mmol), 2-bromo-4-fluoropyridine (0.086 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL) and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0 →100/0) to afford a mixture of the title compound and byproduct (0.0489 g).

Step C

The mixture of the title compound and byproduct from Step B above (0.0489 g) was dissolved in dichloromethane (5 mL) and trifluoroacetic acid (1.5 mL) was added. The reaction mixture was stirred at room temperature for 6 hours. The reaction mixture was diluted with diluted with dichloromethane (50 mL) and water (20 mL). The pH of the aqueous phase was adjusted to pH~12 by the addition of a 1 M aqueous sodium hydroxide solution. The aqueous layer was separated, extracted with dichloromethane (25 mL), the combined organic layer dried over $Na_2SO_4$, filtered and the solvent removed under reduced pressure. The residue was purified by preparative TLC with a loading of ~0.03 g of mixture per 1000 μM Analtech Uniplate (20×20 cm) using dichloromethane/methanol (90/10) as mobile phase to afford the less polar title compound as off-white solid (0.0145 g, 7% for 3 steps) and a more polar mixture of two compounds.

$^1$H NMR (400 MHz, DMSO-$d_6$) δ=9.42 (s, 1H), 8.76 (d, 1H), 8.67 (dd, 1H), 8.35 (d, 1H), 8.27 (d, 1H), 7.67-7.60 (m, 5H), 7.35-7.22 (m, 11H), 6.81 (dd, 1H), 6.60 (d, 1H)

Step D

The less polar title compound from Step C above (0.0145 g, 0.027 mmol) was dissolved in dichloromethane (3 mL) and trifluoroacetic acid (2 mL) was added. The reaction mixture was stirred at room temperature for 18 hours. The reaction mixture was diluted with diluted with dichloromethane (50 mL) and water (20 mL). The pH of the aqueous phase was adjusted to pH~12 by the addition of a 1 M aqueous sodium hydroxide solution. The aqueous layer was separated, extracted with dichloromethane (25 mL), the combined organic layer dried over $Na_2SO_4$, filtered and the solvent removed under reduced pressure. The residue was purified by chromatography on silica (10 g HP-SIL) using a Biotage Isolera system employing a dichloromethane/methanol gradient (100/0→95/5→90/10) to afford the Comparative Example C9 (F-9) as off-white solid (0.0025 g, 33%).

$^1$H NMR (400 MHz, DMSO-$d_6$) δ=12.43 (br-s, 1H), 9.45 (s, 1H), 8.82-8.77 (m, 2H), 8.54 (d, 1H), 8.44 (d, 1H), 8.22 (dd, 1H), 7.53 (d, 1H), 7.46-7.42 (m, 1H)

MS (ESI): m/z=264.63 [M+H]$^+$.

Comparative Example 9 (F-9) Precursor

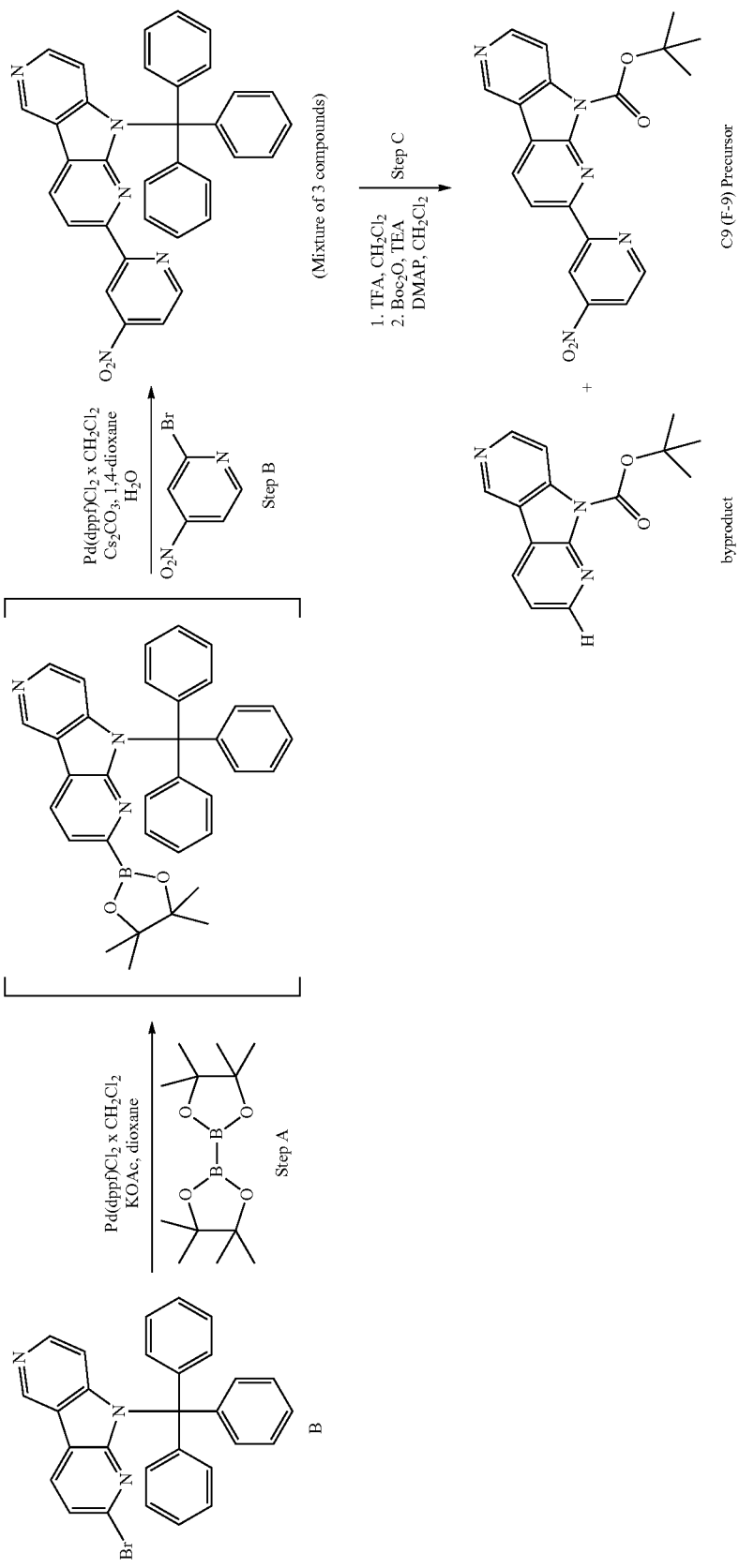

Step A

To a mixture of degassed 1,4-dioxane (8 mL) in a microwave vial was added [1,1-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)ferrocene]dichloro-palladium(II), complex with dichloromethane (0.034 g, 0.04 mmol), 2-bromo-4-nitropyridine (0.1 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL) and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0 →100/0) to afford a mixture of the title compound and byproducts (0.076 g).

Step C

The mixture of the title compound from Step B above and byproducts (0.076 g) was dissolved in dichloromethane (10 mL) and trifluoroacetic acid (2.4 mL) was added. The reaction mixture was stirred at room temperature for 6 hours and then methanol was added (10 mL). The solvents were evaporated in vacuo and the residue suspended in methanol (10 mL). The solvents were again evaporated in vacuo and the residue suspended in dichloromethane (4 mL). After the addition of triethylamine (2 mL, 14.4 mmol), di-tert-butyl dicarbonate (0.2 g, 0.86 mmol), and 4-(dimethylamino)-pyridine (0.0036 g, 0.028 mmol), the reaction mixture was stirred at room temperature for 18 hours. The reaction mixture was diluted with ethyl acetate (100 mL) and water (40 mL). The organic phase was separated, dried over $Na_2SO_4$, filtered and the solvents removed in vacuo. The residue was purified on silica (25 g puriFlash, Interchim) using a Biotage Isolera One purification system employing an ethyl acetate/n-heptane gradient (5/95→100/0→100/0) to afford the Comparative Example C9 (F-9) Precursor and the byproduct as ~1.1-mixture (0.0231 g, pale yellow solid).

$^1$H NMR (400 MHz, CDCl$_3$) δ=9.38 (d, 1H), 9.35 (d, 1H), 9.31 (s, 2H), 9.02 (d, 1H), 8.76-8.70 (m, 5H), 8.68 (d, 1H), 8.55 (d, 1H), 8.43-8.37 (m, 3H), 8.12 (dd, 1H), 8.07 (dd, 1H), 7.43 (d, 1H), 7.41 (d, 1H), 1.82 (s, 18H)

MS (ESI): m/z=291.94 [MH-Boc of the title compound]$^+$, 170.04 [MH$^+$-Boc of byproduct]$^+$ Comparative Example 10 (F-10)

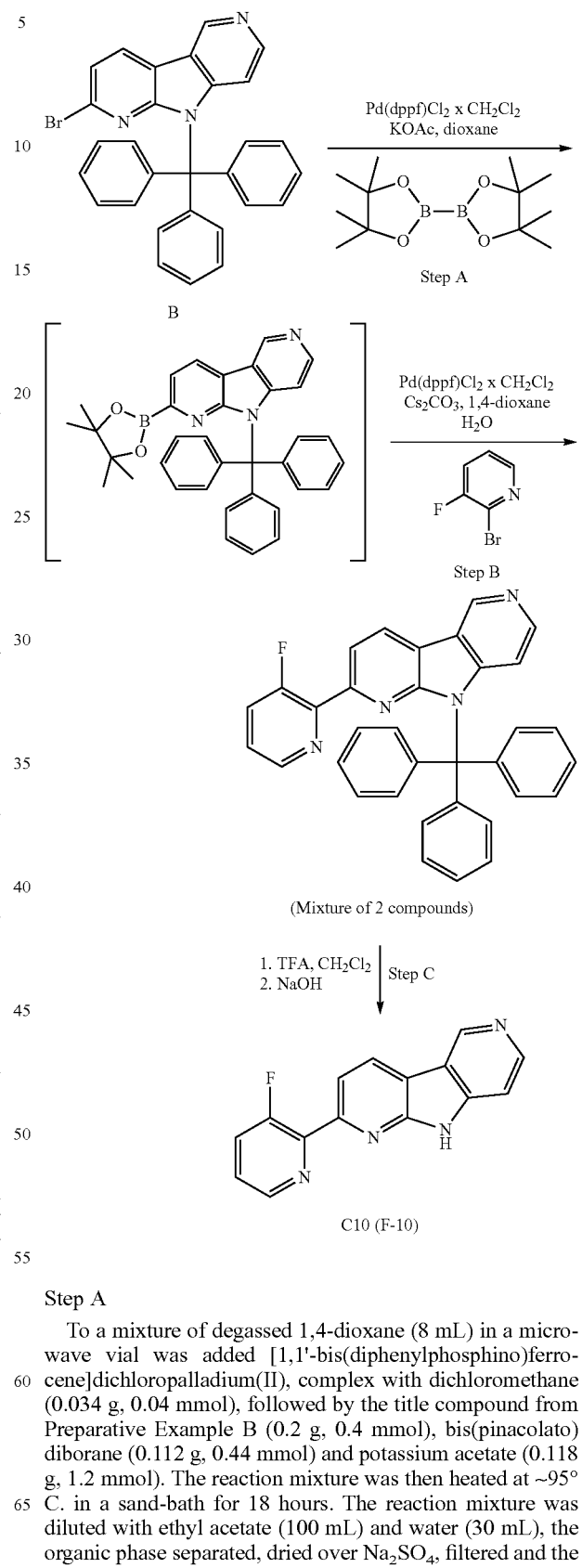

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)ferrocene]dichloro-palladium(II), complex with dichloromethane (0.034 g, 0.04 mmol), 2-bromo-3-fluoropyridine (0.086 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL) and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0 →100/0) to afford a mixture of the title compound and byproduct (0.0586 g).

Step C

The mixture of the title compound and byproduct from Step B above (0.0586 g) was dissolved in dichloromethane (5 mL) and trifluoroacetic acid (1.8 mL) was added. The reaction mixture was stirred at room temperature for 6 hours. The reaction mixture was diluted with diluted with dichloromethane (50 mL) and water (20 mL). The pH of the aqueous phase was adjusted to pH-12 by the addition of a 1 M aqueous sodium hydroxide solution. The aqueous layer was separated, extracted with dichloromethane (25 mL), the combined organic layer dried over $Na_2SO_4$, filtered and the solvent removed under reduced pressure. The residue was purified by chromatography on silica (10 g HP-SIL) using a Biotage Isolera system employing a dichloromethane/methanol gradient (100/0→95/5→90/10) to afford the Comparative Example C10 (F-10) as off-white solid (0.0067 g, 5.7% for 3 steps).

$^1$H NMR (400 MHz, DMSO-d$_6$) δ=12.47 (br-s, 1H), 9.45 (s, 1H), 8.80 (d, 1H), 8.63-8.61 (m, 1H), 8.55-8.53 (m, 1H), 8.00 (d, 1H), 7.94-7.88 (m, 1H), 7.63-7.58 (m, 1H), 7.52 (d, 1H)

MS (ESI): m/z=264.84 [M+H]$^+$.

Comparative Example 10 (F-10) Precursor

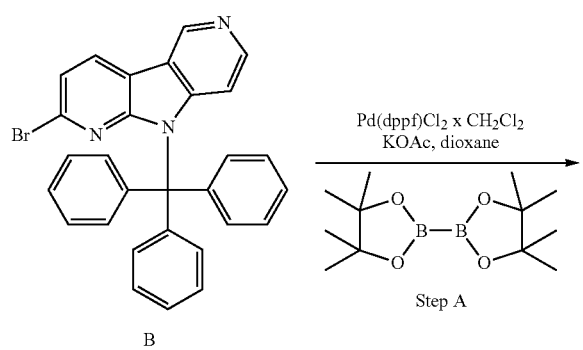

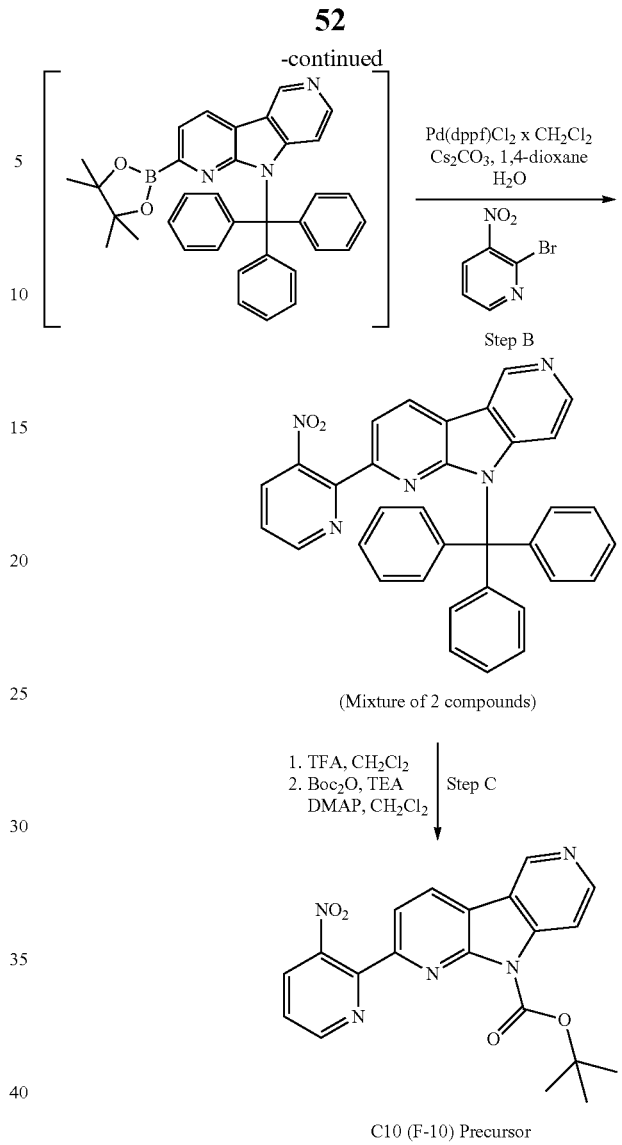

Step A

To a mixture of degassed 1,4-dioxane (8 mL) in a microwave vial was added [1,1'-bis(diphenylphosphino)ferrocene]dichloropalladium(II), complex with dichloromethane (0.034 g, 0.04 mmol), followed by the title compound from Preparative Example B (0.2 g, 0.4 mmol), bis(pinacolato)diborane (0.112 g, 0.44 mmol) and potassium acetate (0.118 g, 1.2 mmol). The reaction mixture was then heated at ~95° C. in a sand-bath for 18 hours. The reaction mixture was diluted with ethyl acetate (100 mL) and water (30 mL), the organic phase separated, dried over $Na_2SO_4$, filtered and the solvents evaporated in vacuo to afford the crude title compound which was directly used in the next step.

Step B

The crude title compound from Step A above was dissolved in a mixture of degassed 1,4-dioxane (8.6 mL) and water (2 mL) in a microwave vial. Then [1,1'-bis(diphenylphosphino)ferrocene]dichloro-palladium(II), complex with dichloromethane (0.034 g, 0.04 mmol), 2-bromo-3-nitropyridine (0.1 g, 0.49 mmol) and cesium carbonate (0.266 g, 0.82 mmol) were added and the reaction mixture was heated at ~115° C. in a sand-bath for 6 hours. The reaction mixture was diluted with ethyl acetate (100 mL)

and water (30 mL), the organic phase separated, dried over $Na_2SO_4$, filtered and the solvents evaporated in vacuo. The dark residue was purified by chromatography on silica (25 g puriFlash, Interchim) using a Biotage Isolera system employing an ethyl acetate/n-heptane gradient (5/95→100/0 →100/0) to afford a mixture of the title compound and byproduct (0.0538 g).

Step C

The mixture of the title compound from Step B above and byproduct (0.0538 g) was dissolved in dichloromethane (4 mL) and trifluoroacetic acid (2.5 mL) was added. The reaction mixture was stirred at room temperature for 16 hours and then methanol was added (10 mL). The solvents were evaporated in vacuo and the residue suspended in methanol (10 mL). The solvents were again evaporated in vacuo and the residue suspended in dichloromethane (4 mL). After the addition of triethylamine (2 mL, 14.4 mmol), di-tert-butyl dicarbonate (0.2 g, 0.86 mmol), and 4-(dimethylamino)-pyridine (0.0036 g, 0.028 mmol), the reaction mixture was stirred at room temperature for 18 hours. The reaction mixture was diluted with ethyl acetate (100 mL) and water (40 mL). The organic phase was separated, dried over $Na_2SO_4$, filtered and the solvents removed in vacuo. The residue was purified on silica (25 g puriFlash, Interchim) using a Biotage Isolera One purification system employing an ethyl acetate/n-heptane gradient (5/95→100/0→100/0) to afford the Comparative Example C10 (F-10) Precursor as pale yellow solid (0.0194 g, 12.1% for 3 steps).

$^1$H NMR (400 MHz, $CDCl_3$) δ=9.35 (d, 1H), 8.90 (d, 1H), 8.73 (d, 1H), 8.58 (d, 1H), 8.24-8.17 (m, 3H), 7.57-7.53 (m, 1H), 1.73 (s, 9H)

MS (ESI): m/z=391.92 [$MH^+$], 291.90 [$MH^+$-Boc]

Synthesis of $^{18}$F-Labeled Compounds

General $^{18}$F-Fluorination Method a (Direct Aromatic $^{18}$F-Fluorination)

The n.c.a [$^{18}$F]fluoride (2-5 GBq) was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, a solution of the dissolved precursor was added to the dried K[$^{18}$F]F-$K_{222}$ complex. The reaction vial was sealed and heated under conventional heating for 15 min at 130° C. Subsequently, the reaction mixture was quenched with water and the crude product was purified via semi-preparative HPLC. The isolated tracer was diluted with water (35 mL), trapped on a C-18 Plus cartridge (Waters), washed with water (5 mL), eluted with ethanol (1 mL) and formulated in saline.

General $^{18}$F-Fluorination Method (Direct $^{18}$F-Labeling Plus Deprotection)

The tracers were synthesized starting from n.c.a. [$^{18}$F]fluoride (1-10 GBq) by a $^{18}$F-direct fluorination. The aqueous [$^{18}$F]fluoride solution was trapped on a Sep-Pak Accell Plus QMA light cartridge (Waters) and eluted with a solution $K_2CO_3$/Kryptofix® 2.2.2. The water was removed using a stream of $N_2$ at 120° C. and co-evaporated to dryness with MeCN (3×1 mL). Afterwards, the respective dissolved precursor was added to the dried K[$^{18}$F]F-$K_{222}$ complex. The reaction vial was sealed and heated for 15 min at 120-160° C. (heating block).

For deprotection hydrochloric acid was added and the mixture was stirred for another 10 min at 110° C. After neutralization using sodium hydroxide solution the reaction mixture was quenched with ammonium formate buffer and trapped on a C-18 Plus cartridge (Waters). The cartridge was washed with water (5 mL), eluted with acetonitrile and subsequently, the crude product was purified via semi-preparative HPLC. The isolated tracer was diluted with water (25 mL), trapped on a C-18 Plus cartridge (Waters), washed with water (5 mL), eluted with ethanol (1 mL) and formulated in saline.

Example $^{18}$F-1

$^{18}$F-1 (680 MBq) was synthesized according to General $^{18}$F-fluorination method A using the corresponding nitro precursor molecule (M. Timothy et al., J. Labelled Comp. Radiopharm. (2013), 56(14), 736-740) (2.8 mg, 7.1 µmol) in dimethyl sulfoxide (0.6 mL).

The radiochemical purity of 100% was determined by analytical reversed-phase HPLC ($t_R$(RAD-trace)=3.19 min). The identity of $^{18}$F-1 was confirmed by comparing the retention time with the non-radioactive reference F-1.

Example $^{18}$F-2

$^{18}$F-2 (680 MBq) was synthesized according to General $^{18}$F-fluorination method A using Comparative Example 2 (F-2) precursor (WO 2015/052105) (3.4 mg, 8.7 µmol) in dimethyl sulfoxide (0.6 mL).

The radiochemical purity of 98% was determined by analytical reversed-phase HPLC ($t_R$(RAD-trace)=3.27 min). The identity of $^{18}$F-2 was confirmed by comparing the retention time with the non-radioactive reference F-2.

Example $^{18}$F-4

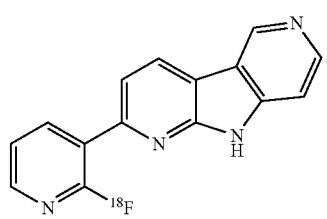

$^{18}$F-4

$^{18}$F-4 (300 MBq) was synthesized according to General $^{18}$F-fluorination method B using precursor molecule compound 14 (3.1 mg, 5.9 µmol) in dimethyl sulfoxide (0.6 mL).

The radiochemical purity of 100% was determined by analytical reversed-phase HPLC ($t_R$(RAD-trace)=3.31 min). The identity of $^{18}$F-4 was confirmed by comparing the retention time with the non-radioactive reference F-4.

Determination of Binding in AD and Healthy Control Brain Homogenates

20 µg of human Alzheimer disease brain homogenate was incubated with a dilution series of each test compound (1000 to 0.06 nM) in the presence of 800 Bq of $^{18}$F-labeled Tau binder. The samples were shaken at 110 rpm for 45 min at 37° C. Samples were then filtered through GF/B 96 well filter plates and washed twice with 300 µL assay buffer (PBS containing 0.1% BSA and 2% DMSO). Thereafter, filter plates were sealed and a Fuji Film Imaging Plate (BAS-SR2025) was placed on top. The imaging plate was analyzed after overnight exposition using a Fuji Film BAS-5000. Non-specific signal was determined with samples containing $^{18}$F-labeled Tau-reference binder in the presence of assay buffer without brain substrate and competitor. Specific binding was calculated by subtracting the non-specific signal from the measured samples signal. The unblocked $^{18}$F- labeled Tau-binder signal was defined as total binding. $IC_{50}$ values were calculated by Prism V6 (GraphPad) setting total binding to 100%.
Results:

High tau-affinity of compounds F-1, F-2, and F-4 was found in a competition assay using human AD brain homogenate. $IC_{50}$ values for Tau binding of <2 nM were measured for all compounds.

A high signal-to-noise ratio between AD brain homogenate and healthy control brain homogenate was obtained with the compound $^{18}$F-4 with a ratio of 10.1. A low signal to noise ratio between AD brain homogenate and healthy control brain homogenate of 1.3 was obtained for compound $^{18}$F-1.

Further data were generated using additional human brain tissues.

The signal-to-noise ratio between AD brain homogenate and healthy control brain homogenate for compound $^{18}$F-4 was determined to be 12.2, 21.0, 27.5 respectively.

Significant lower values were obtained for compound $^{18}$F-1, where those ratios are only 1.7, 1.8 and 2.5.

Also compound $^{18}$F-2 showed significantly lower ratios between the signal in AD brain homogenates and healthy control brain homogenate (3.3, 4.5, 6.9).

Autoradiography in Human Brain Slices 18 micron thick frozen human brain slices and 6 micron thick human FFPE brain slices were examined via autoradiography. Brain sections were equilibrated for at least 1 h in 1×PBS solution prior to use in the experiment. Each brain section was covered with a solution of the $^{18}$F-labeled tracer (200 Bq/µl, 500 µl) in 1×PBS. For blocking experiments with the corresponding $^{19}$F-compound, an excess of the blocking compound (10 µM) was mixed with the $^{18}$F-compound. The brain sections were allowed to incubate with the tracer solution at room temperature for 1 h, drained afterwards and placed in a slide holder. The slides were then washed sequentially with 1×PBS for 1 min; 70% EtOH in 1×PBS for 2 min; 30% EtOH in 1×PBS for 2 min; and 1×PBS for 1 min. The slides were allowed to air-dry before being placed on Fuji imaging plates for 30 min for overnight exposure. The imaging plates were scanned and the signal was measured using Fuji software to produce an autoradiographic image of the brain section.
Results:

Compound $^{18}$F-4 was tested in autoradiography studies using human brain sections (AD, PSP, PiD, HC). Using section from AD brains, a strong punctated staining was detectable that could be blocked with the addition of excess corresponding cold compound. In the healthy control (HC) sections, no specific signal was visible (FIG. 1). Similar results were obtained for compound $^{18}$F-4 on PSP and PiD brain sections.

Determination of the Binding Affinity to Amyloid-Beta in AD Brain Homogenate

20 µg of human Alzheimer disease brain homogenate was incubated with a dilution series of each test compound (1000 to 0.06 nM) in the presence of 800 Bq of $^{18}$F-labeled beta-amyloid binder. The samples were shaken at 110 rpm for 45 min at 37° C. Samples were then filtered through GF/B 96 well filter plates and washed twice with 300 µL assay buffer (PBS containing 0.1% BSA and 2% DMSO). Thereafter, filter plates were sealed and a Fuji Film Imaging Plate (BAS-SR2025) was placed on top. The imaging plate was analyzed after overnight exposition using a Fuji Film BAS-5000. Non-specific signal was determined with samples containing $^{18}$F-labeled beta-amyloid binder in the presence of assay buffer without brain substrate and competitor. Specific binding was calculated by subtracting the non-specific signal from the measured samples signal. The unblocked $^{18}$F-labeled beta-amyloid binder signal was defined as total binding. $IC_{50}$ values were calculated by Prism V6 (GraphPad) setting total binding to 100%.
Results:

Low affinity of compounds F-1, F-2, and F-4 for beta-amyloid was found in a competition assay using human AD brain homogenate. $IC_{50}$ values for beta-amyloid binding of >1 µM were measured for all compounds.

Determination of the Binding Affinity to MAO A in HC Brain Homogenate

20 µg of human brain homogenate (without AD pathology) was incubated with a dilution series of each test compound (1000 to 0.06 nM) in the presence of 800 Bq of $^{18}$F-labeled MAO-A binder ([$^{18}$F]fluoroethyl harmine, FEH). The samples were shaken at 110 rpm for 45 min at 37° C. Samples were then filtered through GF/B 96 well filter plates and washed twice with 300 µL assay buffer (PBS containing 0.1% BSA and 2% DMSO). Thereafter, filter plates were sealed and a Fuji Film Imaging Plate (BAS-SR2025) was placed on top. The imaging plate was analyzed after overnight exposition using a Fuji Film BAS-5000. Non-specific signal was determined with samples containing $^{18}$F-labeled FEH in the presence of assay buffer without brain substrate and competitor. Specific binding was calculated by subtracting the non-specific signal from the measured samples signal. The unblocked $^{18}$F-labeled FEH signal was defined as total binding. $IC_{50}$ values were calculated by Prism V6 (GraphPad) setting total binding to 100%.
Results:

In the mouse brain homogenate, compound F-1 showed a high off-target affinity towards MAO A of 22 nM in the $^{18}$F-FEH competition assay. The affinity of compound F-2 was reduced to 475 nM, whereas off-target affinity to MAO A for compound F-4 was further reduced with $IC_{50}$ values of 1300 nM.

Using human control brain homogenate (healthy control) compound F-1 showed a high off-target affinity towards MAO A of 5 nM in the FEH competition assay. The affinity of compound F-2 was reduced to 100 nM, whereas off-target affinity to MAO A for compound F-4 was further reduced with an $IC_{50}$ value of 530 nM.

Determination of the Binding Affinity to MAO B in HC Brain Homogenate

20 µg of human brain homogenate (without AD pathology) was incubated with a dilution series of each test compound (1000 to 0.06 nM) in the presence of 800 Bq of $^{18}$F-labeled MAO-B binder ([$^{18}$F]fluoro deprenyl). The samples were shaken at 110 rpm for 45 min at 37° C. Samples were then filtered through GF/B 96 well filter plates and washed twice with 300 µL assay buffer (PBS containing 0.1% BSA and 2% DMSO). Thereafter, filter plates were sealed and a Fuji Film Imaging Plate (BAS-SR2025) was placed on top. The imaging plate was analyzed after overnight exposition using a Fuji Film BAS-5000. Non-specific signal was determined with samples containing $^{18}$F-labeled fluoro deprenyl in the presence of assay buffer without brain substrate and competitor. Specific binding was calculated by subtracting the non-specific signal from the measured samples signal. The unblocked $^{18}$F-labeled fluoro deprenyl signal was defined as total binding. $IC_{50}$ values were calculated by Prism V6 (GraphPad) setting total binding to 100%.
Results:

In the human HC brain homogenate, compound F-1 showed a high off-target affinity towards MAO B of 170 nM in the $^{18}$F-labeled fluoro deprenyl competition assay. The affinity of compound F-4 was reduced to values >1000 nM.

PK Studies in Healthy Mice

NMRI mice (weight range 25-35 g) were injected intravenously with the $^{18}$F-labeled compounds. Up to 150 µL of 1×PBS solution with 10%-15% EtOH or dilution medium (57% water for injections, 18% polyethylene glycol 400, 15% ethanol, 10% water) containing the $^{18}$F-labeled compound (2-10 MBq) were injected. Anesthesia with isoflurane was induced before injection of the tracer and maintained during the image acquisition period. PET scans were performed using a SIEMENS INVEON small animal PET/CT scanner (Siemens, Knoxville, Tenn.). PET acquisition was started immediately before the radioactive dose was injected into the animal through the tail vein. Images were generated as dynamic scans for 60 minutes.

Compound $^{18}$F-1: peak uptake: 5.3% ID/g, ratio of uptake peak/30 min: 6.8, brain retention at 60 min: 0.8% ID/g, bone uptake in shoulder joint at 60 min: 4.0% ID/g.

Compound $^{18}$F-2: peak uptake: 5.7% ID/g, ratio of uptake peak/30 min: 10.9, brain retention at 60 min: 0.6% ID/g, bone uptake in shoulder joint at 60 min: 6.2% ID/g.

Compound $^{18}$F-4: peak uptake: 5.8% ID/g, ratio of uptake peak/30 min: 22.0, brain retention at 60 min: 0.2% ID/g, bone uptake in shoulder joint at 60 min: not detectable.

Figure 2:
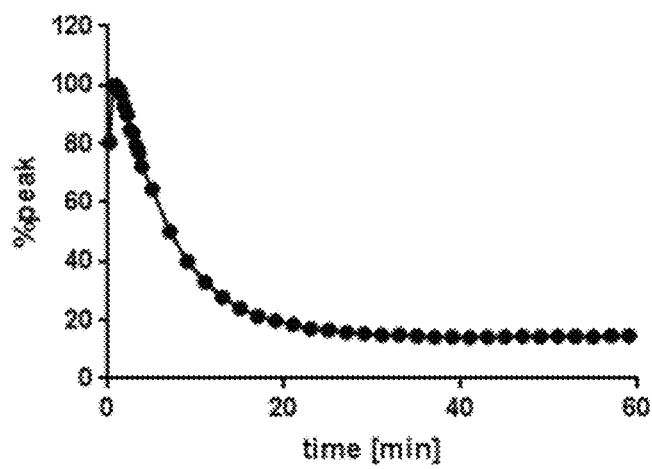
FIG. 2: Washout curves depicting the clearance of the activity from the normal brain for compounds $^{18}F$-1, $^{18}F$-2 and $^{18}F$-4.
Figure 2:
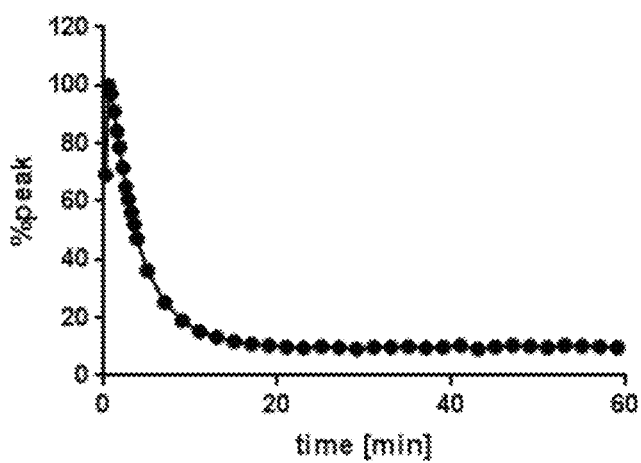
Figure 2:
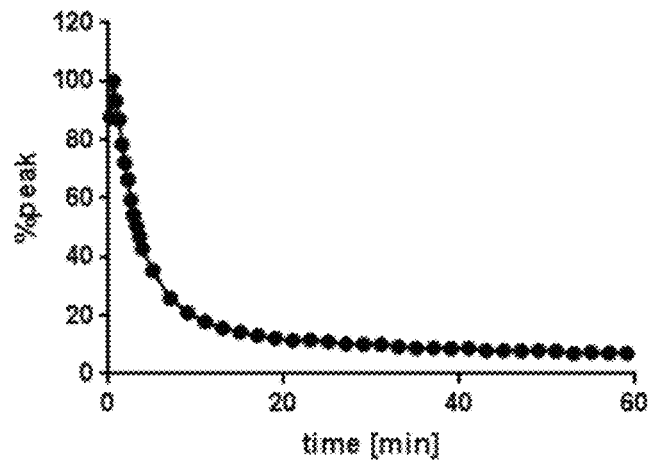

The peak uptake in the brain was set to 100% and washout curves were generated to evaluate the clearance of the activity from the normal brain (FIG. 2).

Human Imaging Study

In a clinical trial, subjects with AD as well as non-demented controls (NDC) underwent dynamic PET imaging for over 3 h following 370 MBq bolus injection of $^{18}$F-4.

Figure 3:
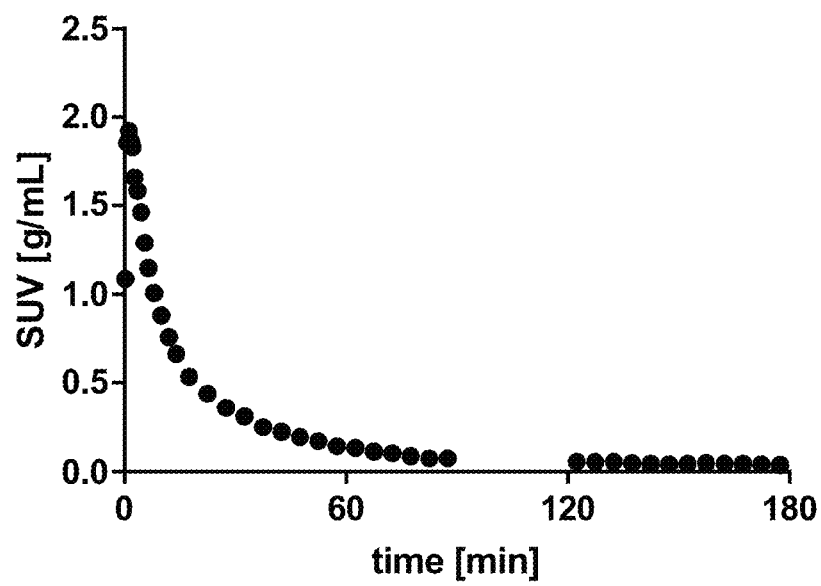
FIG. 3: Brain up-take and wash-out of $^{18}F$-4 in a non-demented human control subject.

Results:

Initial imaging data shows robust brain uptake and fast wash-out in non-target regions. In NDCs, there was no increased uptake seen in choroid plexus, basal ganglia, striatum, amygdala, meninges or other regions noted with other tau agents (FIG. 4a). $^{18}$F-4 shows good brain uptake and fast washout from non-target brain regions (see FIG. 3). In AD, focal asymmetric uptake was evident in temporal, parietal and frontal lobes (FIG. 4b).

TABLE 1

Summary of pre-clinical characteristics

| Criteria for Tau-PET-Imaging agents | Compound $^{18}$F-1 | Compound $^{18}$F-2 | Compound $^{18}$F-4 |
|---|---|---|---|
| High affinity to Tau | +++ | +++ | +++ |
| (IC$_{50}$ in AD brain homogenate)$^{b)}$ | (<2 nM)$^{a)}$ | (<2 nM)$^{a)}$ | (<2 nM)$^{a)}$ |
| Binding to AD and non-AD tauopathies | | | |
| (determined by autoradiography on human brain slices)$^{c)}$ | | | |
| AD brain (Braak stage 5/6) | +++$^{d)}$ | +++$^{e)}$ | +++$^{a)}$ |
| AD brain (Braak stage 1/3) | NA | NA | +++$^{a)}$ |
| PSP | –$^{d)}$ | –$^{e)}$ | +++$^{a)}$ |
| PiD | –$^{d)}$ | –$^{e)}$ | +++$^{a)}$ |
| Low affinity to amyloid-beta | +++$^{a)}$ | +++$^{a)}$ | +++$^{a)}$ |
| (IC$_{50}$ in AD brain homogenate)$^{b)}$ | >1 µM | >1 µM | >1 µM |
| Low affinity to MAO A | – | + | +++ |
| (IC$_{50}$ in mouse brain homogenate)$^{b)}$ | (22 nM)$^{a)}$ | (475 nM)$^{a)}$ | (1300 nM)$^{a)}$ |
| Low affinity to MAO A | – | o | ++ |
| (IC$_{50}$ in HC homogenate)$^{b)}$ | (5 nM)$^{a)}$ | (100 nM)$^{a)}$ | (530 nM)$^{a)}$ |
| Low affinity to MAO B | o | +++ | +++ |
| (IC$_{50}$ in HC homogenate)$^{b)}$ | (170 nM) | (>1000 nM) | (>1000 nM) |
| High signal to noise | – | NA | +++ |
| (Ratio of tracer signal AD brain/signal in HC brain homogenate)$^{c)}$ | 1.3$^{a)}$ | | 10.1$^{a)}$ |
| High signal to noise (further homogenates) | – | o | +++ |
| Ratio of tracer signal in 3 different AD brain homogenates/signal in HC brain homogenates)$^{c)}$ | 1.7, 1.8, 2.5$^{a)}$ | 3.3, 4.5, 6.9$^{a)}$ | 12.2, 21.0, 27.5$^{a)}$ |
| High signal to noise | o | +++ | +++ |
| (Ratio of tracer signal AD brain/signal in mouse brain homogenate)$^{c)}$ | 2.2$^{a)}$ | 15.0$^{a)}$ | 15.1$^{a)}$ |
| Good brain uptake | ++ | ++ | ++ |
| (Tracer uptake in healthy mice after iv injection)$^{c)}$ | (5.3% ID/g)$^{a)}$ | (5.7% ID/g)$^{a)}$ | (5.8% ID/g)$^{a)}$ |
| Fast washout from healthy brain | o | + | +++ |
| (Ratio of tracer uptake at 2 min and 30 min in healthy mice)$^{c)}$ | (6.8)$^{a)}$ | (10.9)$^{a)}$ | (22.0)$^{a)}$ |
| Low retention in healthy brain | – | o | +++ |
| (Tracer signal in healthy mice at 60 min after iv injection)$^{c)}$ | (0.8% ID/g)$^{a)}$ | (0.6% ID/g)$^{a)}$ | (0.2% ID/g)$^{a)}$ |
| Low or minor de-fluorination | o | – | +++ |

TABLE 1-continued

Summary of pre-clinical characteristics

| Criteria for Tau-PET-Imaging agents | Compound $^{18}$F-1 | Compound $^{18}$F-2 | Compound $^{18}$F-4 |
|---|---|---|---|
| (Tracer uptake in bone in healthy mice at 60 min after iv injection)[c] | (4.0% ID/g)[a] | (6.2% ID/g)[a] | (<0.5% ID/g)[a],[f] |

− poor,
o moderate,
+ good,
++ very good,
+++ excellent
[a] in house data, see experimental section above;
[b] determined with the non-radioactive fluorine-19 derivatives F-1, F-2 and F-4;
[c] determined with the radioactive fluorine-18 derivatives $^{18}$F-1, $^{18}$F-2 and $^{18}$F-4;
[d] Marquie et al. 2015;
[e] WO2015/052105;
[f] no de-fluorination detected
NA: not available.

As can be seen from Table 1, the prior art compounds $^{18}$F-1 and $^{18}$F-2 have limitations especially in respect to:
Low binding to Tau-isoforms in non-AD tauopathies,
Affinity for MAO A, and thus low selectivity to Tau,
Not having low signal in healthy brain,
Not having fast washout from healthy brain,
Long-term retention in healthy brain, and/or
in vivo de-fluorination.
On the other hand, compound $^{18}$F-4 shows:
Specific binding to AD and non-AD tauopathy brain slices (examples: strong signal for
PSP, PiD in contrast to the reports for compound $^{18}$F-1),
Less affinity to MAO A in whole mouse brain homogenate (59-fold higher $IC_{50}$ than compound $^{18}$F-1 and 2.7-fold higher $IC_{50}$ than compound $^{18}$F-2),
Less affinity to MAO A in HC brain homogenate (106-fold higher $IC_{50}$ than compound $^{18}$F-1 and 5-fold higher $IC_{50}$ than compound $^{18}$F-2),
Less affinity to MAO B in HC brain homogenate (>5-fold higher $IC_{50}$ than compound $^{18}$F-1),
Higher signal to noise ratio, determined by the binding in AD brain homogenate vs. HC brain homogenate (7.7-fold higher ratio than $^{18}$F-1),
Higher signal to noise ratio, determined by the binding in further AD brain homogenate vs. HC brain homogenate (7.2-11 fold higher than $^{18}$F-1, 3.7-4.0 fold higher ratio than $^{18}$F-2),
Higher signal to noise ratio, determined by the binding in AD brain homogenate vs. whole mouse brain homogenate (6.9-fold higher ratio than $^{18}$F-1),
Faster washout from healthy brain in mice (3.2-fold faster than compound $^{18}$F-1 and 2.0-fold faster than compound $^{18}$F-2),
Lower long-term retention in healthy brain (4-fold less than compound $^{18}$F-1 and 3-fold less than compound $^{18}$F-2),
No de-fluorination in mice (no bone uptake in contrast to 4.0% ID/g for compound $^{18}$F-1 and 6.2% ID/g for compound $^{18}$F-2), Due at least to its high affinity to Tau, its faster brain-washout, lower long-term retention in healthy brain, and/or lower binding affinity to other brain targets, compound $^{18}$F-4 has significantly better properties for determining and quantifying Tau deposits in the brain by positron emission tomography than the prior art compounds $^{18}$F-1 and $^{18}$F-2. In addition to the detection and quantification of Tau deposits in AD, compound $^{18}$F-4 can be useful for clinical evaluation of non-AD tauopathies.

The favorable pre-clinical characteristics of $^{18}$F-4 have been confirmed in human subjects. $^{18}$F-4 shows good brain uptake and fast washout from non-target brain regions (see FIG. 3).

Figure 4:
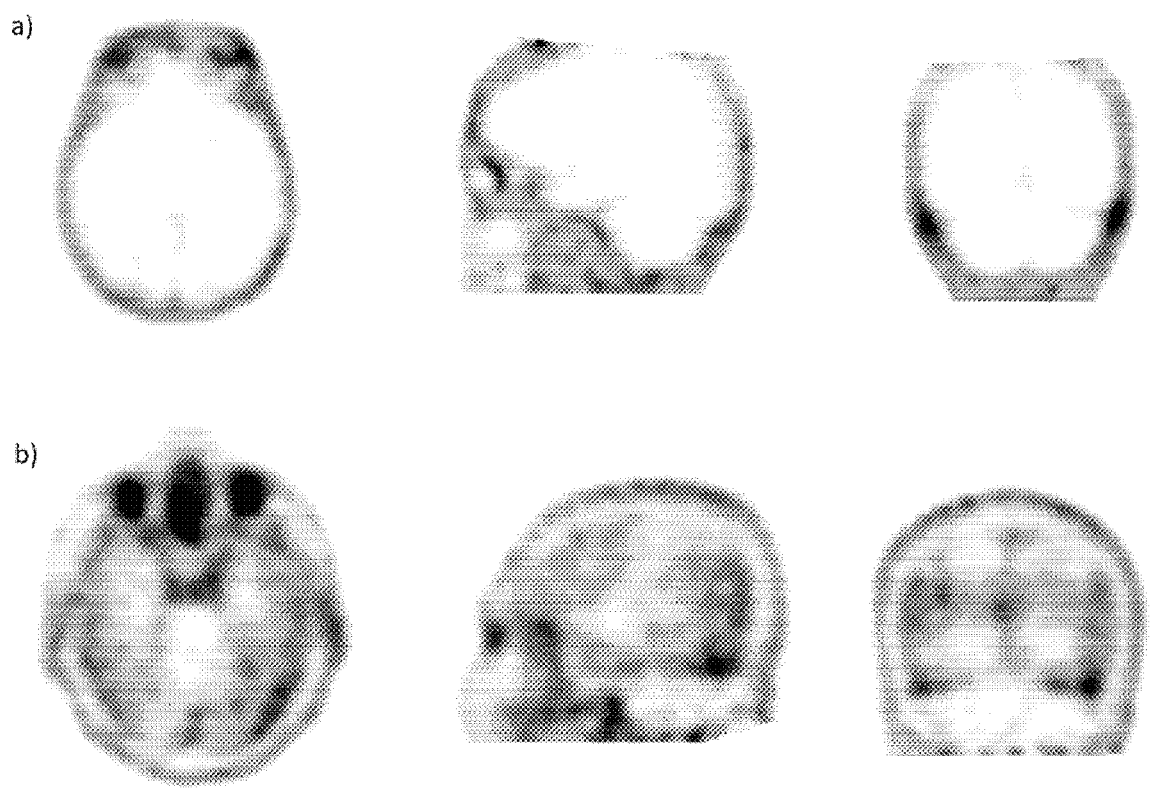
FIG. 4: a)$^{18}F$-4 PET image of a non-demented human control subject with axial, sagittal and coronal projection, b)$^{18}F$-4 PET image of an AD subject with axial, sagittal and coronal projection.

The uptake pattern observed in AD was in accordance with the expected pattern of Tau pathology (FIG. 4).

Surprisingly, $^{18}$F-4 shows significant advantages compared to its regioisomers regarding the key features of a Tau PET imaging tracer (Table 2).

The binding affinity for Tau was poor for the comparative examples 6/$^{18}$F-6 and 10/$^{18}$F-10 and inferior for the comparative examples 5/$^{18}$F-5, 7/$^{18}$F-7 and 9/$^{18}$F-9 ($IC_{50}$ determined in AD brain homogenate).

Inferior selectivity over MAO A was found for the comparative examples 2/$^{18}$F-2, 7/$^{18}$F-7, and 8/$^{18}$F.

The radiolabeling of the comparative examples $^{18}$F-5, $^{18}$F-6, $^{18}$F-8, $^{18}$F-9, and $^{18}$F-10 was inferior (or failed) using standard conditions.

Poor brain uptake in mice was found for comparative example $^{18}$F-10.

The washout in healthy mouse brain was inferior for comparative examples $^{18}$F-5, $^{18}$F-7 and $^{18}$F-10.

De-fluorination in mice was found for the comparative examples $^{18}$F-2, $^{18}$F-5, $^{18}$F-7 and $^{18}$F-10.

TABLE 2

Comparison of regio isomers

| Example | high Tau binding [nM][a,b] | low MAO A binding [nM][a,b,d] | Radio-labeling[a] | Mouse PK | | |
|---|---|---|---|---|---|---|
| | | | | Uptake[a] | Wash-out[a] | De-fluorination[a] |
| 4/$^{18}$F-4 | +++ (<5 nM) | +++ (>1000 nM) | +++ | ++ (5.8% ID/g) | ++ (22) | +++ (<0.5% ID/g)[f] |

TABLE 2-continued

| | Comparison of regio isomers | | | | | |
|---|---|---|---|---|---|---|
| | high Tau | low MAO A | | Mouse PK | | |
| Example | binding [nM]$^{a,b}$ | binding [nM]$^{a,b,d}$ | Radio-labeling$^a$ | Uptake$^a$ | Wash-out$^a$ | De-fluorination$^a$ |
| Comparative example 2/$^{18}$F-2 | +++ (<5 nM) | + (475 nM) | +++ | ++ (5.7% ID/g) | ++ (10.9) | − (6.2% ID/g) |
| Comparative example 5/$^{18}$F-5 | ++ (6.3 nM) | +++ (>1000 nM) | + | ++ (5.3% ID/g) | + (9.6) | + (2.9% ID/g) |
| Comparative example 6/$^{18}$F-6 | − (43 nM) | +++ (>1000 nM) | ○ | +++ (8.2% ID/g) | ++ (14.5) | ○ (4.8% ID/g) |
| Comparative example 7/$^{18}$F-7 | ++ (7.1 nM) | + (268 nM)) | + | +++ (8.5% ID/g) | ○ (7.0) | − (11.1% ID/g) |
| Comparative example 8/$^{18}$F-8 | +++ (<5 nM) | ○ (75 nM) | − | NA | NA | NA |
| Comparative example 9/$^{18}$F-9 | ++ (8.4 nM) | +++ (>1000 nM) | − | NA | NA | NA |
| Comparative example 10/$^{18}$F-10 | − (103 nM) | +++ (>1000 nM) | ○ | ○ (2.1% ID/g) | − (3.6) | − (6.2% ID/g) |

− poor,
○ moderate,
+ good,
++ very good,
+++ excellent
$^a$in house data, see experimental section above;
$^b$determined with the corresponding non-radioactive fluorine-19 derivatives
c) determined with the radioactive fluorine-18 derivatives $^{18}$F-1, $^{18}$F-2 and $^{18}$F-4;
$^d$IC$_{50}$ in mouse brain homogenate
$^f$ no de-fluorination detected
NA: not available.

The invention claimed is:

1. A compound of the formula (I)

as well as pharmaceutically acceptable salts, hydrates, solvates, prodrugs and polymorphs thereof;
wherein R$^1$ is $^{18}$F and R$^2$ is H.

2. A compound of the formula (I)

as well as pharmaceutically acceptable salts, hydrates, solvates, prodrugs and polymorphs thereof; wherein R$^1$ is F and R$^2$ is H.

3. A compound of the formula (I)

as well as pharmaceutically acceptable salts, hydrates, solvates, prodrugs and polymorphs thereof;

R$^1$ is LG, wherein LG is nitro, halogen or trimethyl ammonium;

R$^2$ is H or PG;

PG is a protecting group;

LG is a leaving group.

4. The compound according to claim 3, wherein PG is tert-butyloxycarbonyl (BOC), triphenylmethyl (Trityl) or dimethoxytrityl (DMT).

5. The compound according to claim 2, wherein the compound is detectably labeled with $^2$H, $^3$H.

6. A diagnostic composition comprising a compound as defined in claim 1 and optionally a pharmaceutically acceptable carrier, diluent, adjuvant or excipient.

7. A method of preparing a compound as defined in claim 1 comprising reacting a compound of the formula (I)

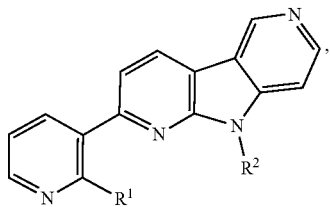

(I)

wherein R¹ is a leaving group (LG) and R² is H or protecting group (PG), with a [$^{18}$F]fluorinating agent, wherein the method further comprises cleaving of the protecting group PG, if present.

8. A kit for preparing a radiopharmaceutical preparation, said kit comprising a sealed vial containing a predetermined quantity of a compound as defined in claim 3.

9. A method of collecting data for the diagnosis of a disorder associated with tau aggregates in a sample or a patient comprising:
  (a) bringing a sample or a specific body part or body area suspected to contain a tau aggregate into contact with a compound as defined in claim 5;
  (b) allowing the compound to bind to the tau aggregate;
  (c) detecting the compound bound to the tau aggregate; and
  (d) collecting data for the diagnosis of the disorder associated with tau aggregates in the sample or the specific body part or body area;
  (e) optionally correlating the presence or absence of compound binding with the tau aggregate with the presence or absence of tau aggregate in the sample or specific body part or body area.

10. A method of determining the amount of tau aggregate in a tissue and/or a body fluid comprising:
  (a) providing a sample representative of the tissue and/or body fluid under investigation;
  (b) bringing the sample into contact with a compound as defined in claim 5;
  (c) testing the sample for the presence of tau aggregate with the compound;
  (d) determining the amount of compound bound to the tau aggregate; and
  (e) calculating the amount of tau aggregate in the tissue and/or body fluid.

11. A method of collecting data for determining a predisposition to a disorder associated with tau aggregates in a patient comprising detecting the specific binding of a compound as defined in claim 5 to a tau aggregate in a sample or in situ which comprises the steps of:
  (a) bringing the sample or a specific body part or body area suspected to contain the tau aggregate into contact with the compound as defined in claim 5, which compound specifically binds to the tau aggregate;
  (b) allowing the compound to bind to the tau aggregate to form a compound/tau aggregate complex;
  (c) detecting the formation of the compound/tau aggregate complex;
  (d) collecting data for determining the predisposition to the disorder associated with tau aggregates in the patient;
  (e) optionally correlating the presence or absence of the compound/tau aggregate complex with the presence or absence of tau aggregate in the sample or specific body part or body area; and
  (f) optionally comparing the amount of the compound/tau aggregate to a normal control value.

12. A method of collecting data for monitoring residual disorder in a patient suffering from a disorder associated with tau aggregates who has been treated with a medicament, wherein the method comprises:
  (a) bringing a sample or a specific body part or body area suspected to contain a tau aggregate into contact with a compound as defined in claim 5, which compound specifically binds to the tau aggregate;
  (b) allowing the compound to bind to the tau aggregate to form a compound/tau aggregate complex;
  (c) detecting the formation of the compound/tau aggregate complex;
  (d) collecting data for monitoring residual disorder in the patient suffering from the disorder associated with tau aggregates who has been treated with the medicament;
  (e) optionally correlating the presence or absence of the compound/tau aggregate complex with the presence or absence of tau aggregate in the sample or specific body part or body area; and
  (f) optionally comparing the amount of the compound/tau aggregate to a normal control value.

13. A method of collecting data for predicting responsiveness of a patient suffering from a disorder associated with tau aggregates and being treated with a medicament comprising:
  (a) bringing a sample or a specific body part or body area suspected to contain an tau aggregate into contact with a compound as defined in claim 5, which compound specifically binds to the tau aggregate;
  (b) allowing the compound to bind to the tau aggregate to form a compound/tau aggregate complex;
  (c) detecting the formation of the compound/tau aggregate complex;
  (d) collecting data for predicting responsiveness of the patient suffering from the disorder associated with tau aggregates and being treated with the medicament;
  (e) optionally correlating the presence or absence of the compound/tau aggregate complex with the presence or absence of tau aggregate in the sample or specific body part or body area; and
  (f) optionally comparing the amount of the compound/tau aggregate to a normal control value.

14. The method of claim 9, wherein the disorder associated with tau aggregates is a tauopathy, Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration, optic nerve drusen, optic neuropathy, optic neuritis, and lattice dystrophy, or atypical parkinsonism.

15. The method of claim 14, wherein the tauopathy is a 3R tauopathy or a 4R tauopathy.

16. The method of claim 9, wherein the body part or body area comprises the brain or the eye.

17. The method of claim 9, wherein the detecting comprises positron emission tomography imaging.

18. A method of collecting data for the diagnosis of a disorder associated with tau aggregates in a sample or a patient comprising:
   (a) bringing a sample or a specific body part or body area suspected to contain a tau aggregate into contact with a compound as defined in claim 1;
   (b) allowing the compound to bind to the tau aggregate;
   (c) detecting the compound bound to the tau aggregate; and
   (d) collecting data for the diagnosis of the disorder associated with tau aggregates in the sample or the specific body part or body area;
   (e) optionally correlating the presence or absence of compound binding with the tau aggregate with the presence or absence of tau aggregate in the sample or specific body part or body area.

19. A method of determining the amount of tau aggregate in a tissue and/or a body fluid comprising:
   (a) providing a sample representative of the tissue and/or body fluid under investigation;
   (b) bringing the sample into contact with a compound as defined in claim 1;
   (c) testing the sample for the presence of tau aggregate with the compound;
   (d) determining the amount of compound bound to the tau aggregate; and
   (e) calculating the amount of tau aggregate in the tissue and/or body fluid.

20. A method of collecting data for determining a predisposition to a disorder associated with tau aggregates in a patient comprising detecting the specific binding of a compound as defined in claim 1 to a tau aggregate in a sample or in situ which comprises the steps of:
   (a) bringing the sample or a specific body part or body area suspected to contain the tau aggregate into contact with the compound as defined in claim 1, which compound specifically binds to the tau aggregate;
   (b) allowing the compound to bind to the tau aggregate to form a compound/tau aggregate complex;
   (c) detecting the formation of the compound/tau aggregate complex;
   (d) collecting data for determining the predisposition to the disorder associated with tau aggregates in the patient;
   (e) optionally correlating the presence or absence of the compound/tau aggregate complex with the presence or absence of tau aggregate in the sample or specific body part or body area; and
   (f) optionally comparing the amount of the compound/tau aggregate to a normal control value.

21. A method of collecting data for monitoring residual disorder in a patient suffering from a disorder associated with tau aggregates who has been treated with a medicament, wherein the method comprises:
   (a) bringing a sample or a specific body part or body area suspected to contain a tau aggregate into contact with a compound as defined in claim 1, which compound specifically binds to the tau aggregate;
   (b) allowing the compound to bind to the tau aggregate to form a compound/tau aggregate complex;
   (c) detecting the formation of the compound/tau aggregate complex;
   (d) collecting data for monitoring residual disorder in the patient suffering from the disorder associated with tau aggregates who has been treated with the medicament;
   (e) optionally correlating the presence or absence of the compound/tau aggregate complex with the presence or absence of tau aggregate in the sample or specific body part or body area; and
   (f) optionally comparing the amount of the compound/tau aggregate to a normal control value.

22. A method of collecting data for predicting responsiveness of a patient suffering from a disorder associated with tau aggregates and being treated with a medicament comprising:
   (a) bringing a sample or a specific body part or body area suspected to contain an tau aggregate into contact with a compound as defined in claim 1, which compound specifically binds to the tau aggregate;
   (b) allowing the compound to bind to the tau aggregate to form a compound/tau aggregate complex;
   (c) detecting the formation of the compound/tau aggregate complex;
   (d) collecting data for predicting responsiveness of the patient suffering from the disorder associated with tau aggregates and being treated with the medicament;
   (e) optionally correlating the presence or absence of the compound/tau aggregate complex with the presence or absence of tau aggregate in the sample or specific body part or body area; and
   (f) optionally comparing the amount of the compound/tau aggregate to a normal control value.

23. The method of claim 22, wherein the disorder associated with tau aggregates is a tauopathy, Alzheimer's disease (AD), familial AD, Creutzfeldt-Jacob disease, dementia pugilistica, Down's Syndrome, Gerstmann-Sträussler-Scheinker disease, inclusion-body myositis, prion protein cerebral amyloid angiopathy, traumatic brain injury, amyotrophic lateral sclerosis, Parkinsonism-dementia complex of Guam, non-Guamanian motor neuron disease with neurofibrillary tangles, argyrophilic grain disease, corticobasal degeneration, diffuse neurofibrillary tangles with calcification, frontotemporal dementia with Parkinsonism linked to chromosome 17, Hallervorden-Spatz disease, multiple system atrophy, Niemann-Pick disease type C, pallido-ponto-nigral degeneration, Pick's disease, progressive subcortical gliosis, progressive supranuclear palsy (PSP), subacute sclerosing panencephalitis, tangle only dementia, postencephalitic Parkinsonism, myotonic dystrophy, Tau panencephalopathy, AD-like with astrocytes, certain prion diseases (GSS with Tau), mutations in LRRK2, chronic traumatic encephalopathy, familial British dementia, familial Danish dementia, frontotemporal lobar degeneration, Guadeloupean Parkinsonism, neurodegeneration with brain iron accumulation, SLC9A6-related mental retardation, white matter tauopathy with globular glial inclusions, traumatic stress syndrome, epilepsy, Lewy body dementia (LBD), hereditary cerebral hemorrhage with amyloidosis (Dutch type), mild cognitive impairment (MCI), multiple sclerosis, Parkinson's disease, HIV-related dementia, adult onset diabetes, senile cardiac amyloidosis, endocrine tumors, glaucoma, ocular amyloidosis, primary retinal degeneration, macular degeneration, optic nerve drusen, optic neuropathy, optic neuritis, and lattice dystrophy, or atypical parkinsonism.

24. The method of claim 23, wherein the tauopathy is a 3R tauopathy or a 4R tauopathy.

25. The method of claim 18, wherein the body part or body area comprises the brain or the eye.

26. The method of claim 18, wherein the detecting comprises positron emission tomography imaging.

* * * * *